United States Patent
Ren et al.

(10) Patent No.: US 12,131,823 B2
(45) Date of Patent: Oct. 29, 2024

(54) SYSTEM AND METHOD FOR MONITORING PATIENT STATE

(71) Applicant: SHENZHEN MINDRAY BIO-MEDICAL ELECTRONICS CO., LTD., Shenzhen (CN)

(72) Inventors: Jian Ren, Shenzhen (CN); Qiling Liu, Shenzhen (CN); Pengpeng Nie, Shenzhen (CN); Hengxing Xia, Shenzhen (CN); Jian Cen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 586 days.

(21) Appl. No.: 17/361,273

(22) Filed: Jun. 28, 2021

(65) Prior Publication Data
US 2021/0327577 A1    Oct. 21, 2021

Related U.S. Application Data

(63) Continuation of application No. PCT/CN2018/125892, filed on Dec. 29, 2018.

(51) Int. Cl.
G16H 40/67    (2018.01)
A61B 5/00     (2006.01)
(Continued)

(52) U.S. Cl.
CPC .......... *G16H 40/67* (2018.01); *A61B 5/0002* (2013.01); *A61B 5/02055* (2013.01);
(Continued)

(58) Field of Classification Search
CPC ............... G16H 40/67; G16H 40/20
(Continued)

(56) References Cited

U.S. PATENT DOCUMENTS

2011/0288379 A1    11/2011   Wu et al.
2012/0056746 A1*   3/2012    Kaigler ............... A61B 5/0022
                                                        702/19
2016/0374588 A1    12/2016   Shariff et al.

FOREIGN PATENT DOCUMENTS

CN    101791214 A    8/2010
CN    102232828 A    11/2011
(Continued)

OTHER PUBLICATIONS

International Search Report issued in corresponding International Application No. PCT/CN2018/125892, mailed Oct. 8, 2019, 4 pages.
(Continued)

*Primary Examiner* — Nadia A Mahmood
(74) *Attorney, Agent, or Firm* — BAYES PLLC

(57) ABSTRACT

A patient state monitoring system and a method for monitoring patient state are disclosed. The patient state monitoring system includes a monitoring device and a monitoring module communicationally connected to the monitoring device, the monitoring module being worn on the patient's body. The patient state monitoring system also includes a processor that obtains parameters, and sets the operating mode of a monitoring module according to the obtained parameters, where the operating mode of the monitoring module comprises a continuous monitoring module and an intermittent monitoring mode. By use of the patient state monitoring system and method, during the monitoring of a patient, strict monitoring of the user's physical condition can be satisfied and the processing of redundant data can be reduced, thereby improving monitoring efficiency and quality.

20 Claims, 8 Drawing Sheets

(51) Int. Cl.
  *A61B 5/0205* (2006.01)
  *A61B 5/318* (2021.01)
  *G16H 10/65* (2018.01)
  *G16H 40/20* (2018.01)
  *G16H 40/40* (2018.01)
  *G16H 50/30* (2018.01)
  *A61B 5/021* (2006.01)
  *A61B 5/08* (2006.01)
  *A61B 5/11* (2006.01)
  *A61B 5/145* (2006.01)

(52) U.S. Cl.
  CPC ............ *A61B 5/318* (2021.01); *G16H 10/65* (2018.01); *G16H 40/20* (2018.01); *G16H 40/40* (2018.01); *G16H 50/30* (2018.01); *A61B 5/021* (2013.01); *A61B 5/08* (2013.01); *A61B 5/11* (2013.01); *A61B 5/14542* (2013.01)

(58) Field of Classification Search
  USPC .......................................................... 600/301
  See application file for complete search history.

(56) References Cited

FOREIGN PATENT DOCUMENTS

| | | |
|---|---|---|
| CN | 103110404 A | 5/2013 |
| CN | 104391561 A | 3/2015 |
| CN | 104739424 A | 7/2015 |
| CN | 106934215 A | 7/2017 |
| CN | 107045766 A | 8/2017 |
| CN | 207429097 U | 6/2018 |
| CN | 108261176 A | 7/2018 |
| CN | 108577828 A | 9/2018 |
| WO | 2017133589 A1 | 8/2017 |

OTHER PUBLICATIONS

First Office Action issued in related Chinese Application No. 201880100209.1, mailed Feb. 28, 2024, 10 pages.

* cited by examiner

SYSTEM AND METHOD FOR MONITORING PATIENT STATE

CROSS-REFERENCE TO RELATED APPLICATION

This disclosure is a continuation of Patent Cooperation Treaty Application No. PCT/CN2018/125892, filed on Dec. 29, 2018, which is hereby incorporated by reference in its entirety.

TECHNICAL FIELD

The present application relates to the field of electronics technologies, and in particular to a patient status monitoring system and method.

BACKGROUND

As the Internet has been gradually gaining popularity and has been widely applied in all walks of life, especially in the medical field, major hospitals have been currently committed to the construction of rehabilitation departments, with the intention of smoothing a transition between critically ill patients and general patients, which is a sub-intensive transitional care unit. Min Wang in the Department of Rehabilitation, Tongji Hospital, Tongji Medical College of Huazhong University of Science and Technology, published a paper pointing out that since the establishment of a sub-intensive transitional care unit, a total of 149 patients have been admitted and 136 (95.8%) cases of them have reached the standard for transfer to a general rehabilitation ward, with the stay time of 1 day to 112 days and of 58.0 days on average; and 13 (4.2%) cases have been transferred to other departments for treatment. Of 52 patients with a tracheotomy, 49 (94.2%) cases had their tracheotomy tubes successfully removed. ADL scores of 136 patients rose from 16.6 (the score when they are admitted to the ward) to 16.9. The patients' family members were able to master the methods of dressing and undressing the patients, scrubbing, grooming, and feeding the patients, skin care, methods of turning over, care of indwelling tubes, care of urine and feces, switching between wheelchairs and flatcars, assisting the patients in walking and going up and down stairs, etc. During the period of stay, of 148 patients with indwelling gastric tubes, 3 cases (2.0%) had accidental extubation. There were no accidents, mistakes, and disputes such as falling from bed, tumbling, scalding, people missing, and suicide. The patient satisfaction rate was 95.8%.

Patients in a sub-intensive transitional care unit need more attention than those in a general ward, but less attention than those in an intensive care unit, for the purposes of speeding up the rehabilitation of the patients and ensuring that the patients have accidents during the rehabilitation process. A monitoring device in the prior art, due to its onefold monitoring mode, cannot meet various needs of patients in a sub-intensive transitional care unit during the rehabilitation process. In addition, real-time monitoring is still used when the patients do rehabilitation exercises, and a large amount of ineffective data is collected, resulting in unnecessary waste of resources. Therefore, it is necessary to provide a new type of physiological monitoring system to meet the needs of the sub-intensive transitional care unit.

SUMMARY

Embodiments of the present application provide a patient status monitoring system and method. According to the embodiments of the present application, a continuous monitoring mode and a discontinuous monitoring mode are set, and switching is performed between the two monitoring modes as required according to collected monitoring-related data of a patient, such that while the patient is adequately monitored, an electronic system can reduce the processing of redundant data and improve the efficiency and quality of monitoring.

According to a first aspect, an embodiment of the present application provides a patient status monitoring system, comprising a monitoring device and a monitoring module communicatively connected to the monitoring device, wherein the monitoring module is worn on the body of a patient and comprises: a processor configured to obtain a parameter, and set a working mode of the monitoring module according to the obtained parameter, wherein the working mode of the monitoring module comprises a continuous monitoring module and a discontinuous monitoring mode.

According to a second aspect, an embodiment of the present application provides a patient status monitoring method, applied to a patient status monitoring system comprising a monitoring device and a monitoring module communicatively connected to the monitoring device, the monitoring module being worn on the body of a patient and comprises a processor, wherein the method comprises:

obtaining, by the processor, a parameter, and setting a working mode of the monitoring module according to the obtained parameter, wherein the working mode of the monitoring module comprises a continuous monitoring module and a discontinuous monitoring mode.

According to a third aspect, an embodiment of the present application provides a computer-readable storage medium storing a plurality of program instructions, wherein the plurality of program instructions are to be invoked by a processor to perform any one of the methods described above.

According to the patient status monitoring system and method, and the computer-readable storage medium disclosed in the disclosure, a parameter is obtained, and then a working mode of a monitoring module is set according to the obtained parameter. Because the working mode of the monitoring module comprises a continuous monitoring mode and a discontinuous monitoring mode, and frequency of the continuous monitoring mode is greater than frequency of the discontinuous monitoring mode, the patient status monitoring system can adjust the monitoring mode in real time according to monitoring-related data of the patient, to provide better monitoring quality for the patient. In addition, the system can reduce the processing of redundant data and improve the efficiency of monitoring.

BRIEF DESCRIPTION OF THE DRAWINGS

In order to more clearly describe the technical solutions in the embodiments of the present application or in the prior art, the drawings required for describing the embodiments or the prior art will be briefly described below. Apparently, the drawings in the following description show only some of the embodiments of the present application, and those of ordinary skill in the art may still derive other drawings from these drawings without creative efforts.

DETAILED DESCRIPTIONS

The technical solutions in the embodiments of the disclosure will be clearly and completely described below in conjunction with the accompanying drawings in the embodiments of the disclosure. Apparently, the embodiments described are merely some rather than all of the embodiments of the disclosure. Based on the embodiments in the disclosure, all other embodiments derived by those of ordinary skill in the art without creative efforts shall all fall within the scope of protection of the disclosure.

Figure 1:
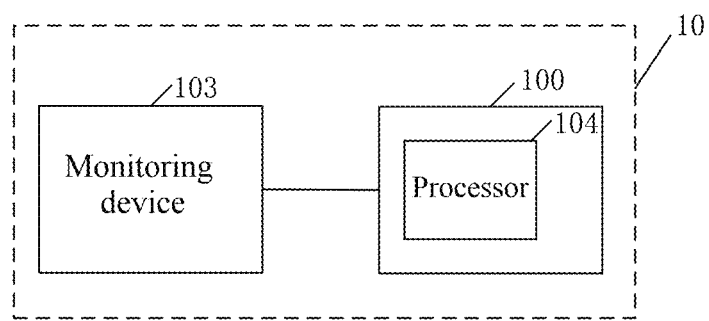
FIG. 1 is a structural diagram of a patient status monitoring system according to an embodiment of the present application.

FIG. 1 is a structural diagram of a patient status monitoring system according to an embodiment of the present application, comprising a monitoring device and a monitoring module communicatively connected to the monitoring device, wherein the monitoring module is worn on the body of a patient and comprises: a processor configured to obtain a parameter, and set a working mode of the monitoring module according to the obtained parameter, wherein the working mode of the monitoring module comprises a continuous monitoring module and a discontinuous monitoring mode. Frequency of the continuous monitoring mode is greater than frequency of the discontinuous monitoring mode, wherein the frequency comprises measurement frequency of the monitoring module and/or frequency of data transmission between the monitoring device and the monitoring module, and the frequency of the continuous monitoring mode being greater than the frequency of the discontinuous monitoring mode comprises at least one of the following two conditions: measurement frequency of the monitoring module in the continuous monitoring mode is greater than measurement frequency of the monitoring module in the discontinuous monitoring mode, and frequency of data transmission in the continuous monitoring mode is greater than frequency of data transmission in the discontinuous monitoring mode.

Figure 2:
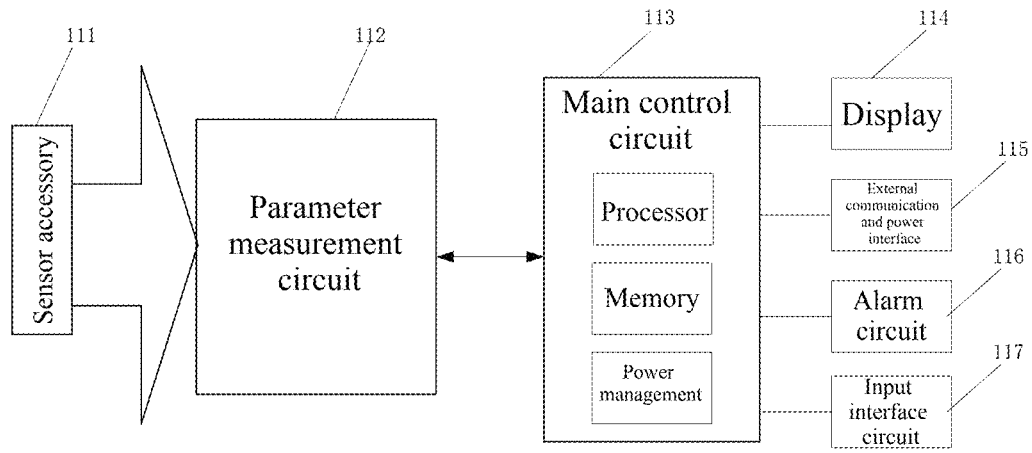
FIG. 2 is a system framework diagram of a monitoring device or monitoring module according to an embodiment of the present application.

As shown in FIG. 2, the present application provides a system framework diagram of a monitoring device or monitoring module. The monitoring device or module component comprises at least a parameter measurement circuit 112. The parameter measurement circuit 112 comprises at least one parameter measurement circuit corresponding to a physiological parameter. The parameter measurement circuit comprises at least one parameter measurement circuit in an electrocardiogram (ECG) parameter measurement circuit, a respiratory parameter (RESP) measurement circuit, a body temperature parameter (TEMP) measurement circuit, a blood oxygen parameter (SpO2) measurement circuit, a non-invasive blood pressure parameter (NIBP) measurement circuit, an invasive blood pressure parameter measurement circuit, etc. Each parameter measurement circuit is connected to an externally inserted sensor accessory 111 through a corresponding sensor interface. Sensor accessories 111 comprise corresponding detection accessories for the detection of a physiological parameter such as electrocardiogram, respiration, blood oxygen, blood pressure, and body temperature. The parameter measurement circuit 112 is mainly used to connect the sensor accessories 111 to obtain the collected physiological parameter signals, and may comprise measurement circuits for at least two types of physiological parameters. The parameter measurement circuit may be, but is not limited to, a physiological parameter measurement circuit (module), a human physiological parameter measurement circuit (module), a sensor for collecting human physiological parameters, etc. Specifically, the parameter measurement circuit obtains a physiological sampled signal related to a patient from an external physiological parameter sensor accessory through the extended interface, and processes the physiological sampled signal to obtain physiological data for issuing an alarm and display. The extended interface may be further used to output a control signal that is output from a main control circuit for collecting the physiological parameters to an external physiological parameter monitoring accessory through a corresponding interface, achieving the monitoring and control of the physiological parameters of the patient.

The monitoring device or monitoring module may further comprise a main control circuit 113. The main control circuit 113 needs to comprise at least one processor and at least one memory. Certainly, the main control circuit 113 may further comprise at least one of a power management module, a power IP module, an interface conversion circuit, etc. The power management module is configured to control the power on and off of an entire machine, a power-on sequence of each power domain inside a board card, and battery charging and discharging. The power IP module is a separate power module firmed by associating a principle diagram of a power supply circuit unit that is frequently and repeatedly invoked, with a PCB layout. That is, an input voltage is converted into an output voltage through a predetermined circuit, wherein the input voltage and the output voltage are different. For example, the voltage of 15 V is converted into 1.8 V, 3.3 V, 3.8 V, etc. It can be understood that the power IP module may be single-channel or multi-channel. When the power IP module is single-channel, the power IP module can convert one input voltage into one output voltage. When the power IP module is multi-channel, the power IP module can convert one input voltage into a plurality of output voltages, and voltage values of the plurality of output voltages may be the same or different, such that different voltage requirements of a plurality of electronic components can be met at the same time. In addition, the module has few external interfaces, and works in the system as a black box decoupled from an external hardware system, which improves the reliability of the entire power system. The interface conversion circuit is configured to convert a signal output by a main control minimum system module (i.e., at least one processor and at least one memory in the main control circuit) into an input standard signal required to be received by an actual external device. For example, supporting an external VGA display function is to convert an RGB digital signal output by a main control CPU into a VGA analog signal, and supporting an external network function is to convert an RMII signal into a standard network differential signal.

In addition, the monitoring device or monitoring module may further comprise one or more of a local display 114, an alarm circuit 116, an input interface circuit 117, and an external communication and power interface 115. The main control circuit 113 is configured to coordinate and control various board cards, circuits, and devices in a plurality of monitoring devices or monitoring modules. In this embodiment, the main control circuit 113 is configured to control data interaction and control signal transmission between the parameter measurement circuit 112 and a communication interface circuit, and transfer the physiological data to the display 114 for display, or may receive an entered user control instruction from a touchscreen or a physical input interface such as a keyboard and keys, and certainly may also output a control signal for collecting the physiological parameters. The alarm circuit 116 may be an audible and visual alarm circuit. The main control circuit 113 completes the calculation of physiological parameters, and may send calculation results and waveforms of the parameters to the main unit (such as a main unit with a display, a PC, and a central station) through the external communication and power interface 115. The external communication and power interface 115 may be one or a combination of local area network interfaces composed of Ethernet, a token ring, a token bus, and an optical fiber distributed data interface (FDDI) as the backbone of these three networks, or may be one or a combination of wireless interfaces such as infrared, Bluetooth, Wi-Fi, and WMTS communication, or may be one or a combination of wired data connection interfaces such as RS232 and USB. The external communication and power interface 115 may also be one of a wireless data transmission interface and a wired data transmission interface or a combination thereof. The main unit may be any computer device such as the main unit of the monitor, an electrocardiograph, an ultrasonic diagnosis instrument, a computer, etc., and a monitoring device can be formed by installing matching software. The main unit may alternatively be a communication device such as a mobile phone, and a multi-parameter monitor or module component sends, by using a Bluetooth interface, data to the mobile phone supporting Bluetooth communication, so as to implement remote transmission of the data.

Figure 3:
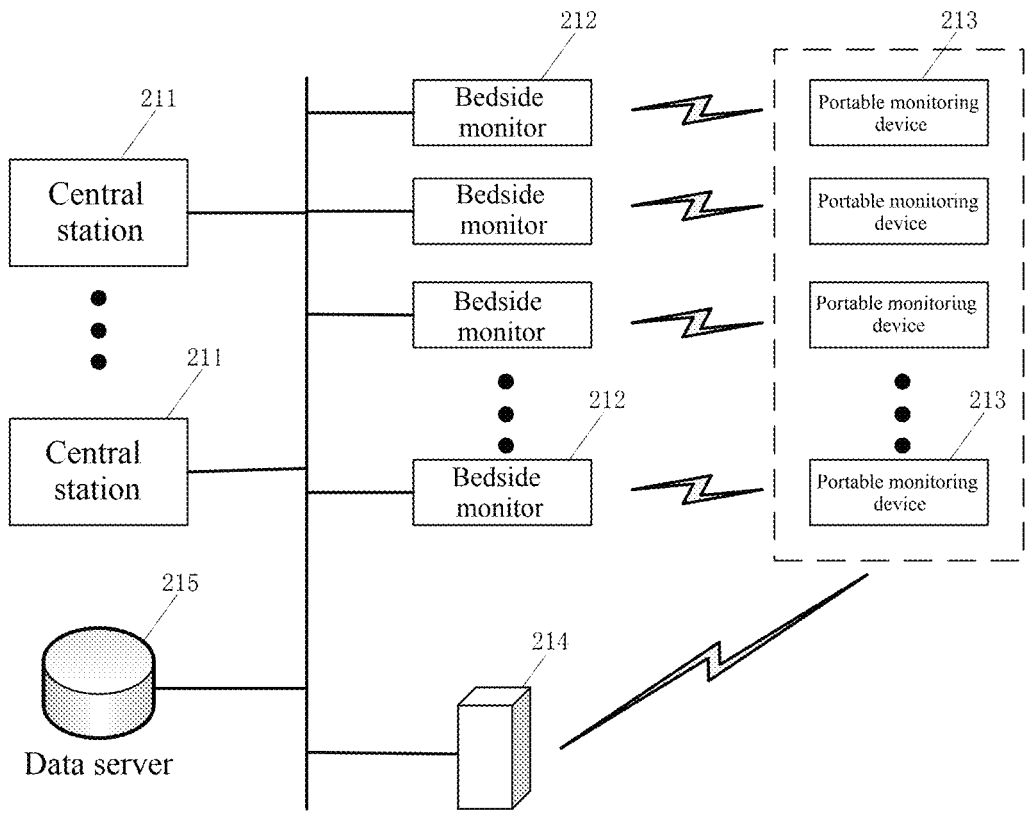
FIG. 3 is a monitor networking system used in a hospital according to an embodiment of the present application.

As shown in FIG. 3, a monitor networking system used in a hospital is provided. By using the system, data of a monitoring device may be stored as a whole to centrally manage patient information and nursing information that are stored in association, which facilitates storage of historical data and alarming in association. In the system shown in FIG. 3, the monitoring device is a bedside monitor 212, and a monitoring module is a portable monitoring device 213. A bedside monitor 212 may be provided for each hospital bed. The bedside monitor 212 may be the above multi-parameter monitor or a plug-in monitor. In addition, each bedside monitor 212 may further be paired with one portable monitoring device 213 for transmission. The portable monitoring device 213 provides a simple and portable multi-parameter monitor or module component, and can be worn on the body of a patient to perform mobile monitoring for the patient. After the portable monitoring device 213 and the bedside monitor 212 perform wireless communication, physiological data generated through mobile monitoring may be transmitted to the bedside monitor 212 for display, or transmitted, by using the bedside monitor 212, to a central station 211 for a doctor or a nurse to check, or transmitted to a data server 215 for storage by using the bedside monitor 212. In addition, the portable monitoring device 213 may further directly transmit, by using a wireless network node 214 arranged in the hospital, the physiological data generated through mobile monitoring to the central station 211 for storage and display, or transmit, by using the wireless network node 214 arranged in the hospital, the physiological data generated through mobile monitoring to the data server 215 for storage. It can be seen that the data corresponding to the physiological parameter displayed on the bedside monitor 212 may originate from a sensor accessory directly connected to the monitor, or from the portable monitoring device 213, or from the data server.

A monitored parameter of a patient comprises at least one of the following three types of parameters:
- a motor-scale-related parameter, such as walking steps, stride frequency, movement distance, and calories;
- a physiological parameter, such as blood oxygen, blood pressure, pulse rate, body temperature, electrocardiogram, respiration, and other parameters, as well as related statistics and a rate of change of these parameters; and
- a human body status time parameter, for example, a motion-related or sleep-related time parameter that characterizes a human body status, such as a sleep time or a motion time. Specific recovery status parameters of the patient are not limited in this embodiment of the disclosure.

Figure 4:
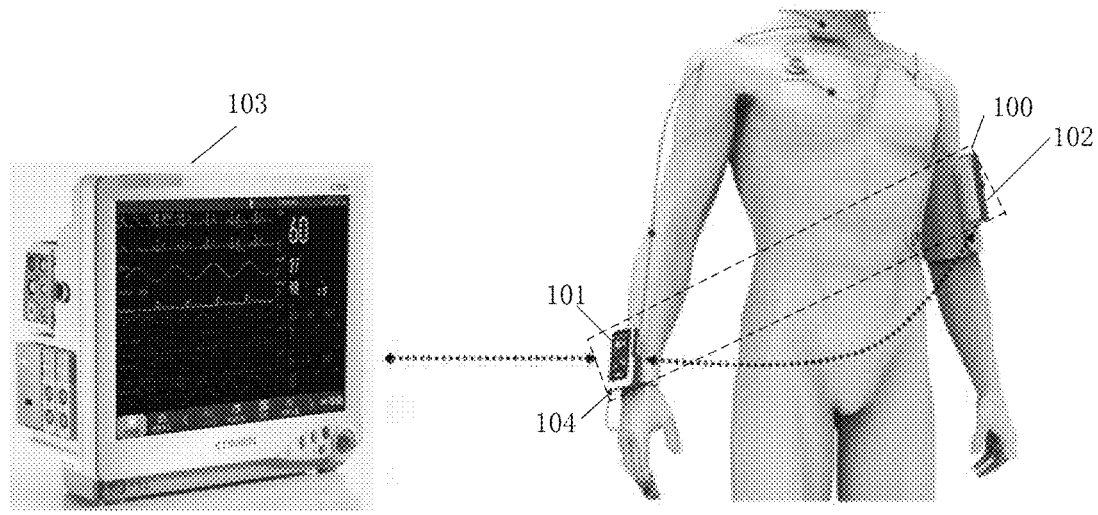
FIG. 4 shows a patient status monitoring system according to an embodiment of the present application.

Referring to FIG. 4, FIG. 4 is a patient status monitoring system 10 according to an embodiment of the present application. The patient status monitoring system comprises a monitoring device 103, a monitoring module 100, and a processor 104 inside the monitoring module 100. The monitoring module 100 is configured to obtain a monitored parameter of a patient and transmit monitoring-related data to the monitoring device 103 by means of wireless communication to complete the monitoring. The processor 104 is configured to set a monitoring mode of the monitoring module according to the monitoring-related data of the monitoring module. The wireless communication may be wireless medical telemetry service (WMTS) communication, near-field communication (NFC), wireless fidelity (Wi-Fi) communication, Bluetooth communication, etc. The WMTS communication mode is specially used for patient status monitoring, with high reliability of obtaining information, but high energy consumption at the same time, which is suitable for the situation where a patient is close to the monitoring device. The Wi-Fi communication mode has low energy consumption and a high coverage rate, which is suitable for the situation where a patient is away from the monitoring device. The NFC communication mode has a short transmission range, but does not require additional network coverage, which is convenient and fast. The monitoring module 100 may comprise at least one POD mobile monitoring module, which is attached to the body of a patient to directly obtain a status parameter of the patient.

When the monitoring module is in the continuous monitoring mode, the monitoring device 103 is a ward-level monitoring device, and the monitoring module 100 communicates with the ward-level monitoring device; and when the monitoring module 100 is in the continuous monitoring mode, the monitoring device 103 is a department-level monitoring device, and the monitoring module 100 communicates with the department-level monitoring device.

The processor 104 being configured to set a monitoring mode of the monitoring module according to the monitoring-related data of the monitoring module specifically comprises:

obtaining a communication mode between the monitoring device and the monitoring module, and switching the working mode of the monitoring module between the continuous monitoring mode and the discontinuous monitoring mode according to a change of the communication mode.

The communication mode comprises at least one of the following: a wireless medical telemetry service (WMTS) mode, a Bluetooth wireless mode, and a Wi-Fi mode.

The processor 104 being configured to set a monitoring mode of the monitoring module according to the monitoring-related data of the monitoring module specifically comprises: when the monitoring device and the monitoring module use the wireless medical telemetry service (WMTS) mode or the Bluetooth wireless mode for communication, the monitoring device is a ward-level monitoring device, and the monitoring module communicates with the ward-level monitoring device; and when the monitoring device and the monitoring module use the Wi-Fi mode for communication, the monitoring device is a department-level monitoring device, and the monitoring module communicates with the department-level monitoring device.

Figure 5:
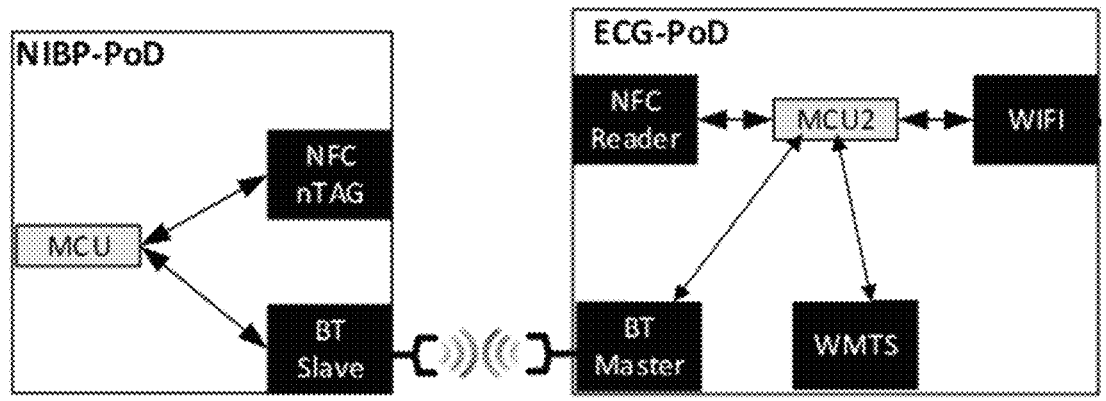
FIG. 5 is a schematic structural diagram of a monitoring module according to the present application.

Optionally, the monitoring module 100 in FIG. 4 comprises two sub-modules: a first monitoring sub-module 101 and a second monitoring sub-module 102, wherein the first monitoring sub-module is an electrocardiogram monitoring module ECG-POD, and the second monitoring sub-module is a non-invasive blood pressure monitoring module NIBP-POD. Referring to FIG. 5, FIG. 5 is a schematic structural diagram of a monitoring module according to the present application. As shown in FIG. 5, the ECG-POD comprises four communication modules: NFC, Bit Torrent (BT), WMTS, and Wi-Fi, and two microcontroller units MCU 1 and MCU 2; and the NIBP-POD comprises two communication modules: NFC and BT, and one microcontroller unit MCU. The ECG-POD and the NIBP-POD can be paired using NFC, and then perform BT transmission. The ECG-POD is a main control module for receiving monitoring-related data of the patient that is collected by the NIBP-POD. In addition, the ECG-POD further comprises a WMTS communication module and a Wi-Fi communication module, and may use WMTS or Wi-Fi to communicate with the monitoring device 103. The MCU 1 and the MCU 2 in the ECG-POD may be used as the processor 104 in FIG. 4, to process the monitoring-related data of the patient that is collected by the monitoring module.

Figure 6:
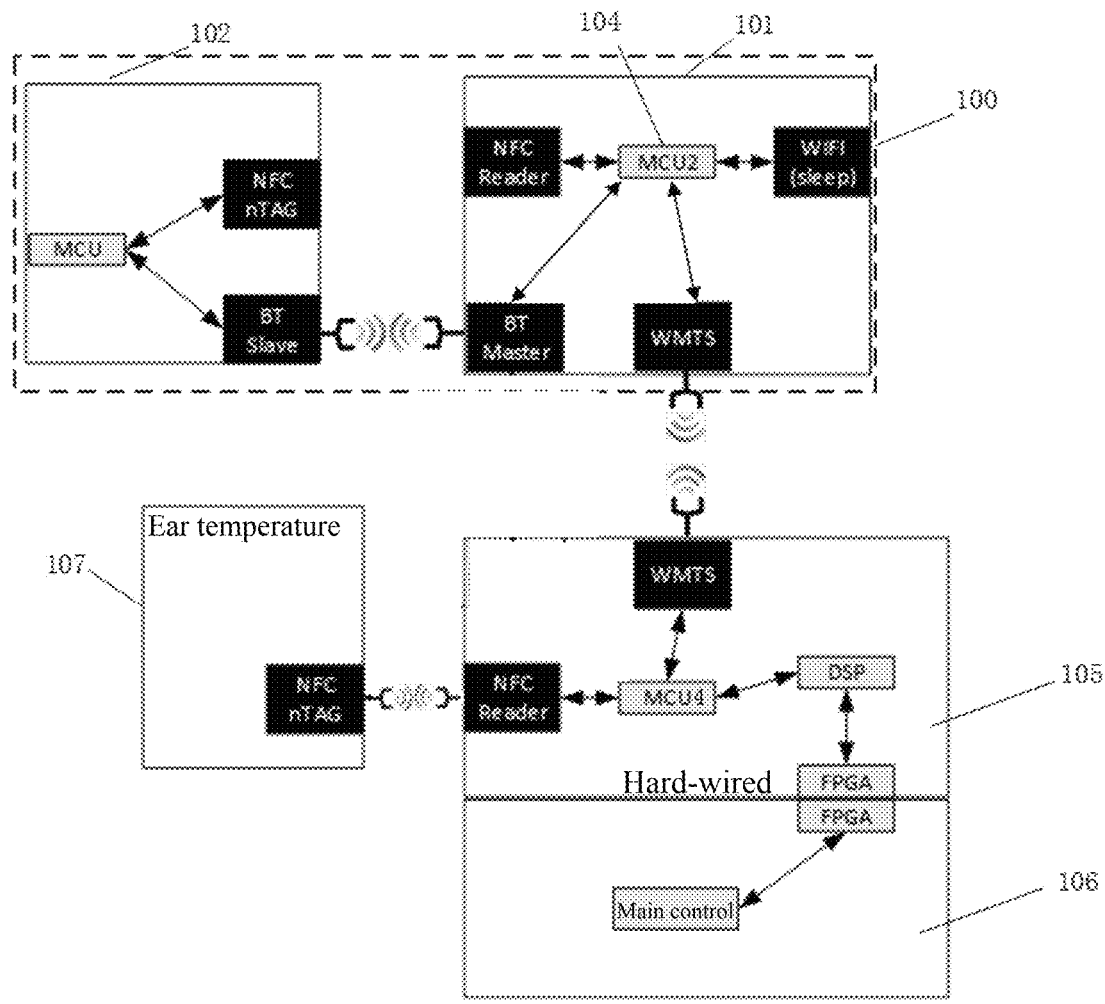
FIG. 6 is a schematic structural diagram of a patient status monitoring system according to an embodiment of the present application.

In addition, referring to FIG. 6, FIG. 6 is a schematic structural diagram of a patient status monitoring system according to an embodiment of the present application. As shown in FIG. 6, the monitoring device may be formed by a receiving box 105 and a monitor 106 that are hard-wired through a parameter slot. The receiving box 105 comprises a WMTS communication module and an NFC communication module, as well as a microcontroller unit MCU 4 and a digital signal processing (DSP) module. The receiving box 105 further performs a circuit connection to the monitor 106 by using a field-programmable gate array (FPGA). The monitor 106 comprises a main control unit for reprocessing or displaying the data transmitted by the receiving box 105.

With the aid of the receiving box 105, the ECG-POD and the monitor implement a one-to-one interconnection through WMTS. The ECG-POD transmits the data to the receiving box 105 through WMTS. After computing the data, the receiving box 105 transfers, in a hard-wired manner through the parameter slot, the data to the main control unit for display. Values such as a heart rate calculated by the receiving box 105 will also be transmitted to the ECG-POD through WMTS for synchronous display. The receiving box 105 is an extension box having a communication module. The extension box can be detachably secured onto the main unit of the monitor. In addition, the extension box can also be connected to other monitoring modules such as an ear temperature measurement module 107 through NFC communication. The extension box further comprises an accommodating space for accommodating a mobile monitoring module such as the ECG-POD.

In another optional embodiment, the main control module ECG-POD may be mounted on a charging pile of a bedside device for charging and detecting, and real-time transmission of medical data at the same time. Then, in this case, the extension box and the ECG-POD can achieve transmission of real-time detection data through a wired or wireless near-field communication channel. For example, the ECG-POD may be inserted into a slot of a plug-in box for charging and data transmission at the same time. Alternatively, the ECG-POD monitoring module may have two separate parts: A front-end collection and communication sending module for a vital sign parameter is physically separated from a back-end information processing module and communication receiving module. In this case, the back-end information processing module and communication receiving module may be inserted into the plug-in box as an independent extended module to achieve charging, data transmission, etc.

Figure 7:
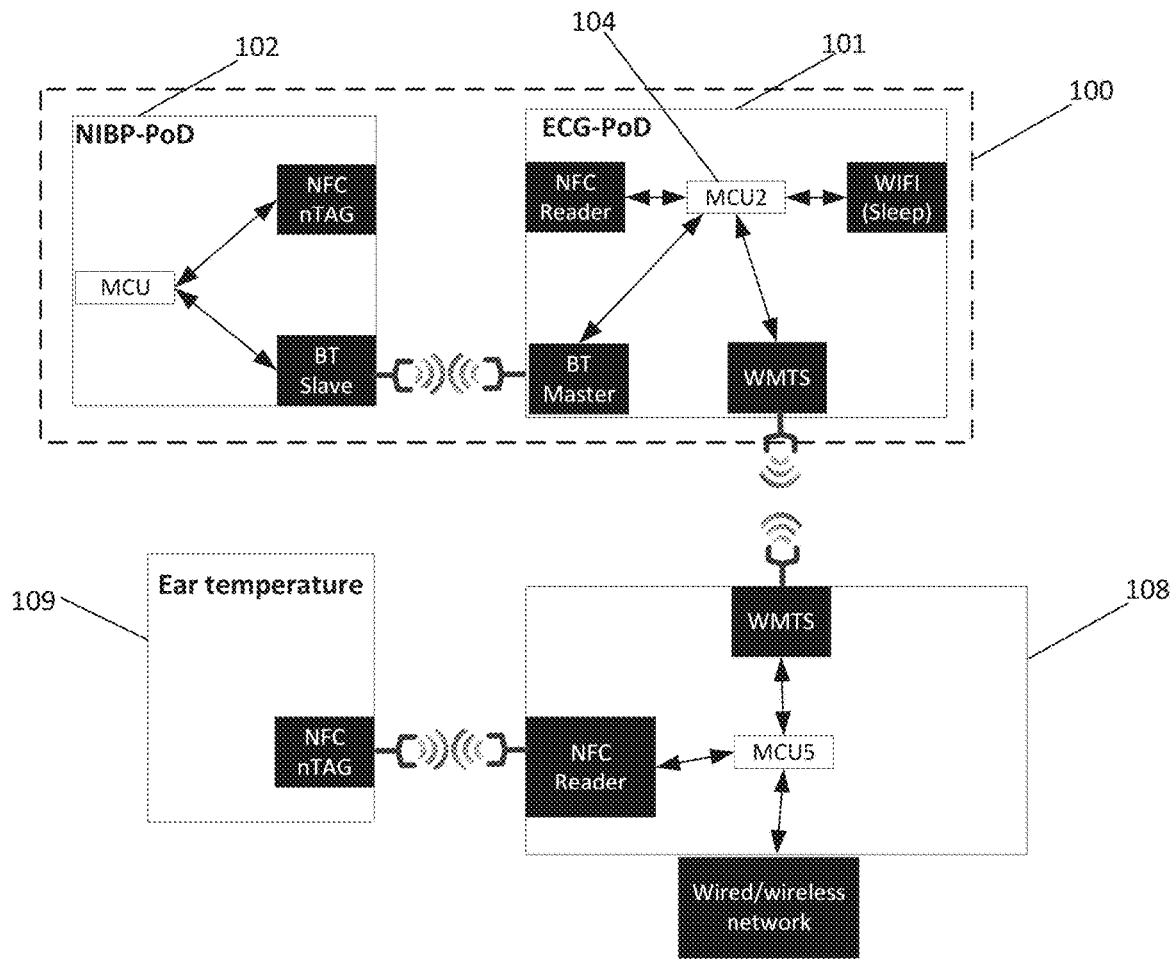
FIG. 7 is a schematic structural diagram of another patient status monitoring system according to an embodiment of the present application.

Optionally, referring to FIG. 7, FIG. 7 is a schematic structural diagram of another patient status monitoring system according to an embodiment of the present application. As shown in FIG. 7, the monitoring device is a bedside DOCK station 108, which may be a bedside plug-in box structure with a plurality of extended module slots and can be mounted beside the bed, or on the bed, or on the wall, or on the bedside centralized station. Its internal structure comprises a NFC communication module and a WMTS communication module, as well as a MCU 5. The communication modules may be built-in or external, or may be configured into independent extended modules. An extended module having a communication function is inserted into the bedside DOCK station, to implement communication with the main control module ECG-POD in the monitoring module. There may be other additional extended modules, such as an ear temperature measurement module 109. The bedside DOCK station may transmit data of the additional extended module to the ECG-POD for data processing and display, or the ECG-POD may transmit the data of the additional extended module to a remote device for data processing, and then a result is fed back to the ECG-POD for display, or a feedback is not returned to the ECG-POD. In this case, a local display of the ECG-POD will play the primary display role, and a processor of the ECG-POD combines the centralized analysis and processing of the data of the monitoring module 100 and the data collected by the ear temperature measurement module 109.

Figure 8:
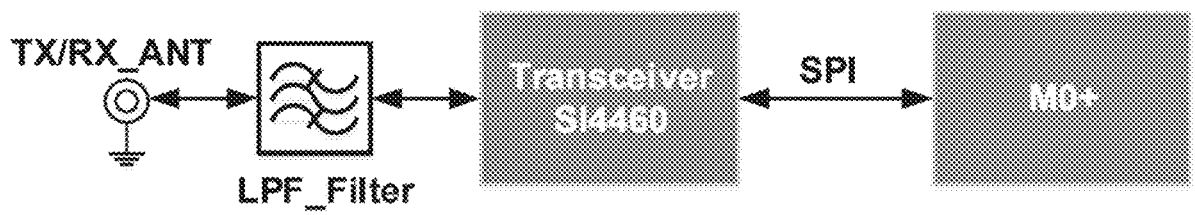
FIG. 8 is a diagram of a WMTS wireless topology of an ECG-POD transmitter according to an embodiment of the present application.
Figure 9:
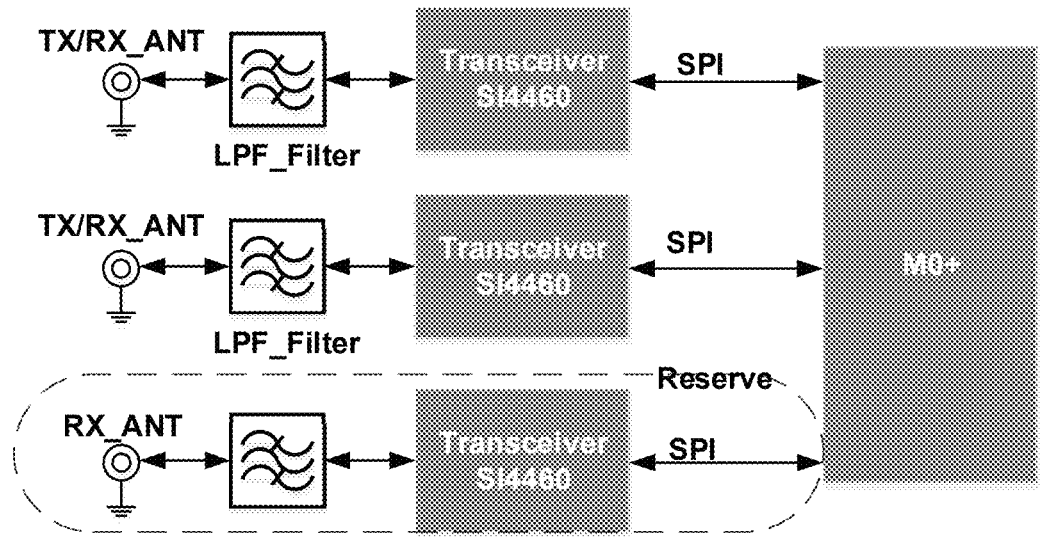
FIG. 9 is a diagram of a WMTS wireless topology of a receiving box according to an embodiment of the present application.

Optionally, when the ECG-POD and the monitoring device are connected through WMTS, referring to FIG. 8 and FIG. 9, FIG. 8 provides a diagram of a WMTS wireless topology of an ECG-POD transmitter, and FIG. 9 provides a diagram of a WMTS wireless topology of a receiving box. The ECG-POD uses only one chip for sending and receiving, but in order to improve the reliability of the uplink, two chips are used for receiving at the receiving box, and M0+ selects correct data received from the two chips each time. When the receiving box performs sending, only one chip works. A half-duplex working mode is maintained between the ECG-POD and the receiving box to achieve two-way communication. One uplink packet is followed by one downlink packet. A radio frequency chip is reserved at the receiving box, mainly for the purpose of scanning spatial signal strength, to study the feasibility of free frequency modulation.

In addition, because WMTS communication is a special frequency band for medical use and has the advantage of good privacy, when the patient is in the ward, WMTS may be used for the communication connection between the ECG-POD and the monitoring device. However, meanwhile, it is necessary to consider the anti-interference problem for a plurality of pairs of paired devices when using the WMTS communication.

Optionally, a frequency division multiplexing WMTS technology is used. Specifically, rules for using frequency division multiplexing are as follows: a group of specific frequencies are used in the same area or in the same department; different frequencies are used for different devices in the same area or the same department, and non-intermodulation interference frequencies are selected for the frequencies; in different areas or different departments, the same frequency group can be used within a distance greater than a first distance threshold; otherwise, different non-intermodulation frequency groups are used; and in order to prevent the mixed use of devices previously deployed in different areas and resulting interference and failure of more devices to transmit data properly, when a device is powered on, full-channel scanning is performed to check whether the device is in a correct frequency group. If the device is in the correct frequency group, data transmission is to be performed normally; and if the device is not in the correct frequency group, no data transmission is to be performed. In order to solve the uniqueness of a device connection at the same moment, devices in point-to-point communication need to regenerate a unique pairing code during the connection, and check the pairing code during a transmission gap, to prevent incorrect devices from being connected and causing a data error or data crosstalk.

Figure 10:
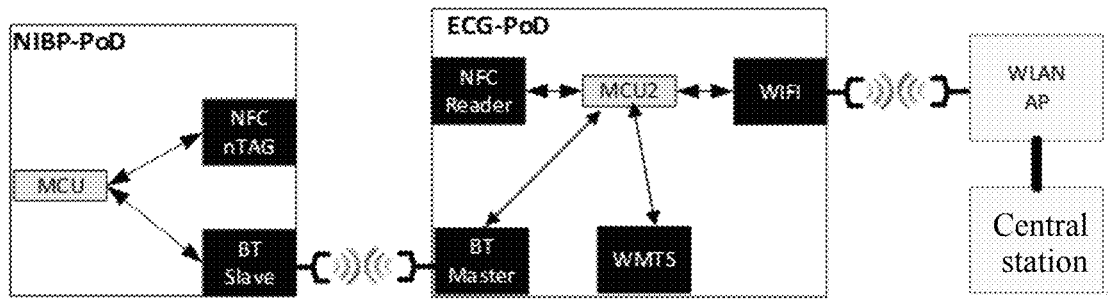
FIG. 10 is a schematic structural diagram of another patient status monitoring system according to an embodiment of the present application.
Figure 11:
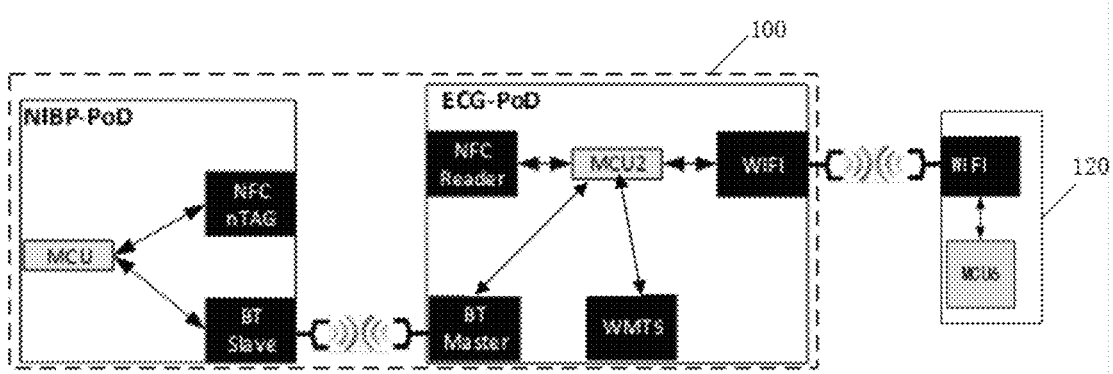
FIG. 11 is a schematic structural diagram of another patient status monitoring system according to an embodiment of the present application.

In another optional embodiment, when the patient is outside the ward and there is no WMTS signal coverage, the patient status monitoring system can switch to a Wi-Fi connection mode. Referring to FIG. 10, FIG. 10 is a schematic structural diagram of another patient status monitoring system according to an embodiment of the present application. As shown in FIG. 10, an ECG-POD is connected to a wireless access point (AP) using Wi-Fi, and then the AP sends data to a central station. The central station may perform data transmission with a monitoring device through Wi-Fi transmission, or perform data transmission with the monitoring device through wired network communication, thereby completing state monitoring for a patient. Alternatively, referring to FIG. 11, FIG. 11 provides a schematic structural diagram of another patient status monitoring system. As shown in FIG. 11, an ECG-POD may also be directly connected to a monitoring device using Wi-Fi, such that even if a patient is outside the ward, the ECG-POD can communicate with the monitoring device in the ward, and send data to the monitoring device.

Optionally, an additional 3G/4G/5G network communication module may further be configured for a mobile monitoring module 100, and a 3G/4G/5G network communication module is configured for a DOCK station on an ambulance at the same time. The DOCK station and the mobile monitoring module 100 use a 3G/4G/5G network for communication transmission, and the DOCK station may further upload data to a hospital-level central station in real time using the 3G/4G/5G network.

Optionally, while the additional 3G/4G/5G network communication module is configured for the mobile monitoring module, an additional 3G/4G/5G network communication module is configured for the ambulance, and the additional 3G/4G/5G network communication module of the ambulance is used as an independent accessory for integrated setting with a main control module in the mobile monitoring module 100. Data collected by the mobile monitoring module may be uploaded to the hospital-level central station in real time using the 3G/4G/5G network communication module. It can be understood that, other mobile communication networks may also be possible, and the above-mentioned communication networks are not limiting, provided that data transmission can be performed using these mobile communication networks.

According to the foregoing embodiment, it can be learned that in the patient status monitoring system, the monitoring module and the monitoring device or other devices can be connected in a wireless communication mode, and available wireless communication modes comprise WMTS, Wi-Fi, Bluetooth, NFC, etc. In the process of wireless communication, due to changes in the distance between the patient and the hospital bed, changes in the patient's physical condition, changes in the patient's motion state, etc., a monitoring mode for the patient's physical condition needs to be switched accordingly, to better monitor the patient.

Optionally, a parameter comprises a monitored parameter of the patient and a status parameter of a device.

Specifically, the patient status monitoring system obtains the monitored parameter of the patient using the monitoring module, the monitored parameter comprising monitoring duration, a physiological parameter of the patient, monitored image display, etc. Alternatively, the status parameter of the device is obtained using the monitoring module, wherein the status parameter of the device may be a status parameter of the monitoring device or a status parameter of the monitoring module, and may be an electricity quantity, storage space, a communication mode, or the like of the device.

Optionally, the monitoring module further comprises: a parameter measurement unit configured to detect a physiological parameter of the patient, wherein the monitored parameter of the patient comprises the physiological parameter.

When obtaining the monitored parameter of the patient, the processor may obtain the physiological parameter of the patient. In addition, the monitoring module may comprise a parameter measurement unit for directly obtaining the physiological parameter of the patient and then transferring same to the processor; or the processor may be directly connected to a sensor attached to the patient to obtain the physiological parameter of the patient. The physiological parameter of the patient comprises blood pressure, blood oxygen, or a heart rate.

Optionally, in terms of the obtaining a parameter, and setting a working mode of the monitoring module according to the obtained parameter, the processor is specifically configured to: obtain the physiological parameter from the parameter measurement unit, wherein the physiological parameter comprises an electrocardiogram (ECG), blood oxygen (SPO2), body temperature (TEMP), and/or blood pressure (NIBP); determine a condition of the patient according to the physiological parameter, wherein the condition comprises good or critical; and set, when the condition is good, the working mode of the monitoring module to the continuous monitoring mode; or set, when the condition is critical, the working mode of the monitoring module to the discontinuous monitoring mode.

Specifically, physiological parameters of the patient are all used to reflect the physical condition of the patient, and the condition of the patient can be determined by analyzing the physiological data obtained by the monitoring module. For example, the parameter electrocardiogram is a graph that records periodic fluctuations of the heart. The normal value of the heart rate is 60 to 100. The heart rate being too fast or too slow indicates that the health status of the patient is not good. The blood oxygen SPO2 indicates blood oxygen saturation, which is not lower than 94% under normal circumstances, with SpO2<90% being defined as the indicator of hypoxemia, which indicates that the patient is critically ill and has respiratory failure. Blood pressure higher than 130 is high blood pressure, and blood pressure lower than 70 is low blood pressure. A risk threshold is set for each physiological parameter, and when there is a physiological parameter reaching the risk threshold, it is determined that the condition of the patient is critical. Alternatively, a weight is set for each physiological parameter, and when the weight of a physiological parameter reaching the risk threshold exceeds a preset weight, it is determined that the condition of the patient is critical; otherwise it is determined that the condition of the patient is good. When the condition of the patient is good, the monitoring of the patient can be appropriately relaxed. Therefore, the monitoring mode that can be used in this case is the discontinuous monitoring mode. When the condition of the patient is critical, the monitoring of the patient needs to be more rigorous, and the continuous monitoring mode needs to be used in this case.

Optionally, the monitoring module further comprises: a motion sensor configured to detect a motion parameter of the patient, wherein the monitored parameter of the patient comprises the motion parameter.

The motion sensor can sensitively sense the motion of the patient, and convert a motion signal into an electrical signal to obtain the motion parameter of the patient, which can be used as the monitored parameter of the patient to determine the working mode of the monitoring module. In addition, the motion sensor can be arranged in the monitoring module, or may be used as a separate device that is communicatively connected to the monitoring module to transfer the obtained motion parameter to the monitoring module.

Optionally, in terms of the obtaining a parameter, and setting a working mode of the monitoring module according to the obtained parameter, the processor is specifically configured to: obtain the motion parameter of the patient from the motion sensor, and obtain duration of a motion signal of the patient according to the motion parameter; make a value comparison between the duration of the motion signal and first preset duration, to obtain a comparison result; and set, when the duration of the motion signal is greater than or equal to the first preset duration, the working mode of the monitoring module to the discontinuous monitoring mode; or set, when the duration of the motion signal is less than the first preset duration, the working mode of the monitoring module to the continuous monitoring mode.

In terms of obtaining the motion parameter of the patient from the motion sensor, motion duration, a range of motion, a motion direction, or motion intensity may be obtained, and according to these motion parameters, the duration of the motion signal of the patient can be obtained.

When in a good physical condition, the patient can walk in or outside the ward, and the motion signal lasts for a long time. If the physical condition of the patient deteriorates, the patient can only lie on the bed, or turn over slightly on the bed, and the motion signal lasts for a short time. The value comparison is made between the duration of the motion signal of the patient and the first preset duration, wherein the first preset duration may be 5 min (minutes), 10 min, or 30 min. As the range of motion of the patient is varying, too slight motion may be considered as that the patient is not moving, and only a signal with a relatively large range of motion is counted as the motion signal, and then the duration of the motion signal of the patient is counted. When an interval between two motion signals is greater than a first interval threshold, the motion signals are considered to be discontinuous. Therefore, the duration of the motion signal means duration of a motion signal with a time interval being less than the first interval threshold. When the duration of the motion signal is greater than or equal to the first preset duration, it indicates that the patient is in a good physical condition, and the working mode of the monitoring module is set to the discontinuous monitoring mode; or when the duration of the motion signal is less than the first preset duration, it indicates that the physical condition of the patient is deteriorating or the condition thereof is critical, and the working mode of the monitoring module is set to the continuous monitoring mode.

Optionally, the motion sensor is a three-axis accelerometer, and the motion parameter is acceleration; and before obtaining the duration of the motion signal of the patient, the processor is further configured to determine that the patient is in an outdoor upright motion state, and is specifically configured to: determine that a communication mode of the monitoring module is a Wi-Fi mode; determine, according to the acceleration, that a range of motion of the patient is greater than a first preset range; determine that an included angle between the direction of the acceleration of the accelerometer and the positive direction of the Z-axis is less than a first preset angle, the positive direction of the Z-axis being a downward direction perpendicular to a horizontal plane; and determine that the patient is in the outdoor upright motion state.

Specifically, according to the foregoing embodiment, it can be learned that detecting whether the patient is in a motion state is to confirm that the physical condition of the patient is good. In some cases, even when the patient is in motion in the ward, the range of motion is very small, and it cannot indicate that the patient is in a good physical condition. In addition, if the condition of the patient deteriorates, the patient may need to be carried out of the ward. At this time, according to changes in acceleration, an acceleration sensor determines that the patient is in a motion state, but in fact the patient is not in motion himself or herself. Therefore, before the duration of the motion signal of the patient is obtained, it is also required to determine that the patient is in a motion state, which actually confirms that the patient is in a good physical condition. First, it is determined that the communication mode of the monitoring module is the Wi-Fi mode, so as to determine that the patient is outside the ward. Then, according to data collected by the accelerometer worn by the patient, it is determined that the range of motion of the patient is greater than the first preset range. Finally, it is determined that the included angle between the direction of the acceleration of the accelerometer and the positive direction of the Z-axis is less than the first preset angle, the positive direction of the Z-axis being the downward direction perpendicular to the horizontal plane. It is determined that the patient is in a self-directed upright motion state, and thereby it is determined that the patient is in a good physical condition at this time.

In another optional embodiment, the monitoring mode for the physical condition of the patient may be switched according to changes in the motion state of the patient. Specifically, the patient status monitoring system measures a physiological sign parameter of the patient using the monitoring module, wherein the physiological sign parameter comprises at least one of a blood pressure parameter, a blood oxygen parameter, an electrocardiogram parameter, and a respiratory parameter. The motion parameter of the patient is obtained using the motion sensor. A posture of the patient is determined according to the motion parameter. The monitoring module adjusts the working mode of the monitoring module according to the posture of the patient. The processor controls the monitoring module to perform measurement for the patient according to the working mode. Specifically, the processor adjusting the working mode of the monitoring module according to the posture of the patient comprises: obtaining measurement frequency according to the posture of the patient, querying a corresponding working mode according to the measurement frequency, and adjusting the corresponding working mode to the working mode of the monitoring module, wherein the working mode is set according to different measurement frequencies. The working mode of the monitoring module 10 comprises at least: the continuous monitoring mode and the discontinuous monitoring mode, wherein in the continuous monitoring mode, the monitoring module performs measurement for the patient at preset first measurement frequency; and in the discontinuous monitoring mode, the monitoring module performs measurement for the patient at preset second measurement frequency, the first measurement frequency being greater than the second measurement frequency. In another embodiment of the present application, in the continuous monitoring mode, the monitoring module performs measurement for the patient at preset first measurement frequency; and in the discontinuous monitoring mode, the monitoring module measures the electrocardiogram and/or blood oxygen of the patient at preset second measurement frequency, and measures the respiration and/or blood pressure of the patient at third measurement frequency, the first measurement frequency being greater than the second measurement frequency, and the third measurement frequency being zero. It can be understood that, in the discontinuous monitoring mode in this embodiment, mobile monitoring will reduce measurement frequency of an electrocardiosignal and a blood oxygen signal, and stop the measurement of parameters such as respiration and non-invasive blood pressure. At the same time, an electrocardiogram (ECG) alarm threshold and a blood oxygen alarm threshold of the monitoring module will also be relaxed accordingly. According to the above settings, the monitoring module may select the corresponding measurement frequency according to the posture of the patient, and then find the corresponding working mode according to the measurement frequency; then the monitoring module is adjusted to this mode to measure the physiological parameter, such that the monitoring module can adjust the measurement frequency adaptively according to the posture of the patient. The posture reflects the state of the patient, and therefore the discontinuous monitoring mode may be used when the state of the patient is relatively good, and the physiological state of the patient can be monitored in real time when the state of the patient is relatively poor.

In some embodiments, the posture of the patient comprises standing, lying on the side, and lying on the back, and the processor determines whether the patient is lying on the side, lying on the back, or in an upright state according to the motion parameter, such as the acceleration.

The processor further adjusts the working mode of the monitoring module according to the posture of the patient.

In this embodiment, when it is determined that the body posture is upright, the processor adjusts the working mode of the monitoring module to the discontinuous monitoring mode; and when it is determined that the body posture is lying on the side or lying on the back, the processor adjusts the working mode of the monitoring module to the continuous monitoring mode.

In this embodiment, the monitoring module can directly adjust the working mode according to whether the patient is lying on the side, lying on the back, or in the upright state. When the patient is in the upright state, the patient is in a good condition, and the working mode is adjusted to the discontinuous monitoring mode; and when the patient is lying on the side or lying on the back, it indicates that the patient is in a poor condition or has tumbled, and the working mode is adjusted to the continuous monitoring mode. In the following, how to determine the posture of the patient will be explained in detail.

Figure 12:
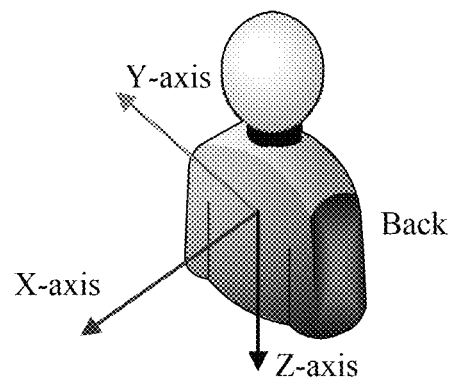
FIG. 12 is a schematic diagram of accelerometer coordinate axes for the body of a patient according to an embodiment of the present application.

Referring to FIG. 12, FIG. 12 is a schematic diagram of accelerometer coordinate axes for the body of a patient according to an embodiment of the present application. As shown in FIG. 12, the positive direction of the X-axis is a forward direction perpendicular to the coronal plane of the human body, the positive direction of the Y-axis is the right direction perpendicular to the sagittal plane of the human body, and the positive direction of the Z-axis is the downward direction perpendicular to the horizontal plane. The range of motion of the patient is calculated, and the formula is as follows:

$$A = \sqrt{x^2 + y^2 + z^2} \tag{1}$$

where A represents the value of the range of motion, and x, y, and z are the values of acceleration in the directions of the X, Y, and Z axes of the accelerometer, respectively.

In addition, included angles between the direction of the acceleration of the accelerometer and the three axial directions can be calculated according to formula (2), and formula (2) is as follows:

$$\begin{cases} \theta_x = \arccos\dfrac{x}{A} \\ \theta_y = \arccos\dfrac{y}{A} \\ \theta_z = \arccos\dfrac{z}{A} \end{cases} \quad (2)$$

where $\theta_x$, $\theta_y$, $\theta_z$ represent the included angles between the direction of the acceleration and the positive directions of the X, Y, and Z axes, respectively. When the included angle between the direction of the acceleration and the positive direction of the Z-axis is less than the first preset angle, the patient is considered to be in the upright state; when the included angle between the direction of the acceleration and the positive direction of the X-axis is less than a second preset angle, the patient is considered to be lying on the back; and when the included angle between the direction of the acceleration and the positive direction of the Y-axis is less than a third preset angle, the patient is considered to be lying on the side.

In this embodiment, it is considered that the patient is in the motion state only when the patient is outside the ward, the range of motion is greater than the first preset range, and the patient is in the upright state. The first preset range is an acceleration value, which may be a value such as 15 m/s² or 20 m/s'. The first preset angle is a small angle such as 5° or 10°.

In other embodiments, the posture of the patient comprises a body pose and body dynamics of the patient, wherein the body pose comprises standing upright, lying on the side, and lying on the back; and body dynamics comprise a motion state and a static state.

The processor is further configured to determine whether the patient is moving and whether the patient is lying on the side, lying on the back, or in the upright state according to the motion parameter, such as the acceleration.

Specifically, the processor is further configured to determine the body pose and body dynamics of the patient. In this embodiment, a method for determining whether the body pose of the patient is lying on the side, lying on the back, or standing upright is the same as that described in the foregoing embodiment, and details are not repeated herein. A method for determining the body dynamics is described below.

Because the accelerometer is a three-axis accelerometer, the processor can use the above formula (1) to calculate the magnitude of the acceleration. When the magnitude is greater than a specified threshold, it can be determined that the patient is in a motion state, and otherwise is in a static state.

$$A = \sqrt{x^2 + y^2 + z^2} \quad (1)$$

For example, the preset threshold is 1.2. If the magnitude of the acceleration is greater than 1.2, it indicates that the patient is moving, that is, in a motion state; and if the magnitude of the acceleration is less than 1.2 and close to 0, it indicates that the patient is basically not moving, that is, in a static state. In this embodiment, the static state may also mean that the patient has a very small range of motion, such as slight shaking. In some embodiments, a preset time period may further be set, and when duration for which the magnitude of the acceleration is greater than the threshold exceeds the preset time period, it is determined that the patient is in a motion state. In this case, when the magnitude of the acceleration is greater than the threshold, but its duration is less than the preset time period, it is still determined that the patient is in a static state. In this embodiment, the body dynamics of the patient is determined according to the magnitude of the acceleration, and the body pose of the patient is determined according to the first, second, and third included angles as described in the first embodiment.

The sequence of determining the body pose and the body state of the patient is not limited.

In a first case, the body dynamics of the patient is first determined, and then the body pose of the patient is determined. In this case, the processor 13 is further configured to: adjust, when the body dynamics of the patient is a static state, the working mode of the monitoring module to the continuous monitoring mode; or adjust, when the body dynamics of the patient is a motion state, the working mode of the monitoring module with reference to the body pose. The adjusting, when the body dynamics of the patient is a motion state, the working mode of the monitoring module with reference to the body pose comprises: adjusting, when it is determined that the body posture is upright, the working mode of the monitoring module to the discontinuous monitoring mode; or adjusting, when it is determined that the body posture is lying on the side or lying on the back, the working mode of the monitoring module to the continuous monitoring mode. Herein, if the patient is in the motion state and is in an upright pose, it indicates that the patient is in a relatively good physical condition and can perform self-directed upright activities. Continuous detection is not needed, and therefore the working mode is adjusted to the discontinuous monitoring mode.

In a second case, the body pose of the patient is first determined, and then the body dynamics of the patient is determined. In this case, the processor 13 is configured to: adjust, when the body pose of the patient is lying on the side or lying on the back, the working mode of the monitoring module to the continuous monitoring mode; or determine, when the body pose of the patient is in an upright state, the working mode with reference to the body dynamics of the patient. The determining, when the body pose of the patient is in an upright state, the working mode with reference to the body dynamics of the patient comprises: when the body dynamics of the patient is a motion state, determining that the working mode is the discontinuous monitoring mode; or when the body dynamics of the monitored object is a static state, determining that the working mode is the continuous monitoring mode.

In a third case, the body pose and the body dynamics of the patient are determined at the same time. In this case, the processor 13 is configured to: adjust, when the body dynamics of the patient is a motion state and the body posture of the patient is upright, the working mode of the monitoring module to the discontinuous monitoring mode; or adjust, when the body dynamics of the patient is a static state and the body posture of the patient is lying on the side or lying on the back, the working mode of the monitoring module to the continuous monitoring mode.

It can be understood that, when the patient is passively pushed out of the ward, the torso of the patient will not have obvious fluctuations in the magnitude of the acceleration. Therefore, in this embodiment, the accelerometer on the torso of the patient is used to determine the range of motion and to further determine whether the patient is in a motion state, such that a self-directed motion of the patient can be identified. The effects achieved by this embodiment is that, when the patient is in a self-directed motion state and the body pose of the patient is in an upright state, it indicates that the patient is moving upright in a self-directed manner. Therefore, the patient is in a good condition, and the working mode can be adjusted to the discontinuous monitoring mode, to perform measurement for the patient at relatively low measurement frequency. Further, depending on the specific condition of the patient, the measurement of some physiological sign parameters of the patient may be stopped, or a heartbeat alarm threshold may be raised, and so on. For example, if the patient is in the recovery period from surgery, but the blood pressure is always normal, when the patient performs normal outdoor activities, the measurement of blood pressure can be temporarily stopped, which can not only ensure the monitoring of the patient, but can also reduce power consumption. In the remaining cases, for example, if the patient is in a static state, the patient may not be able to move independently, or an unexpected situation occurs during the motion, causing the patient to stop moving or to sit down. At this time, the working mode needs to be adjusted to the continuous monitoring mode, and real-time attention is paid to changes in the physiological parameter of the patient. If the patient is lying on the side or lying on the back, similarly, the patient may not be able to move independently, or an unexpected situation occurs during the motion, causing the patient to tumble, etc. The working mode also needs to be adjusted to the continuous monitoring mode, and real-time attention is paid to changes in the physiological parameter of the patient. With the above method, the working mode of the monitoring module is automatically adjusted depending on the actual condition of the patient.

Optionally, the status parameter of the device comprises communication features of the monitoring device and the monitoring module. In an embodiment, the communication feature comprises at least one of the following: a communication mode, communication signal strength, and a packet loss rate. Specifically, the present application provides the following method for setting the monitoring mode according to the communication feature. When the communication mode is a wireless medical telemetry service (WMTS) mode, the working mode of the monitoring module is set to the continuous monitoring mode; or when the communication mode is a wireless fidelity (Wi-Fi) mode, the working mode of the monitoring module is set to the discontinuous monitoring mode. When the communication signal strength is greater than a first signal threshold and the packet loss rate is less than a first preset threshold, the working mode of the monitoring module is set to the continuous monitoring mode; or when the communication signal strength is less than the first signal threshold and the packet loss rate is greater than the first preset threshold, the working mode of the monitoring module is set to the discontinuous monitoring mode. It can be understood that, the monitoring mode may also be determined according to other communication features and other methods, which are not limited herein.

Optionally, the status parameter of the device comprises a distance between the monitoring device and the monitoring module.

The status parameter of the device comprises an attribute parameter and operating parameter of a single device, and may further comprise an association parameter between devices. The distance between the monitoring device and the monitoring module is an association parameter between the devices. The distance between the two may be obtained using a built-in sensor in the monitoring device or the monitoring module, or the distance between the two may be obtained indirectly from other parameters, such as the communication mode or signal strength between the two.

Optionally, in terms of the obtaining a parameter, and setting a working mode of the monitoring module according to the obtained parameter, the processor is specifically configured to: obtain a communication mode between the monitoring module and the monitoring device, wherein the communication mode comprises a wireless medical telemetry service (WA/ITS) mode or a Wi-Fi mode; and use the communication mode as determination data. The distance between the monitoring device and the monitoring module is determined according to the communication mode between the monitoring device and the monitoring module, and when the communication mode is the WA/ITS mode, the monitoring device is close to the monitoring module, and the working mode of the monitoring module is set to the continuous monitoring mode; or when the communication mode is the Wi-Fi mode, the monitoring device is away from the monitoring module, and the working mode of the monitoring module is set to the discontinuous monitoring mode.

Specifically, according to the foregoing embodiment, it can be learned that the distance between the monitoring module and the monitoring device can be reflected by the communication mode between the two. When the communication mode between the monitoring module and the monitoring device is the WA/ITS mode, the monitoring module is close to the monitoring device, which indicates that the patient may be in the ward and is in a poor physical condition and needs more rigorous monitoring. Therefore, the working mode of the monitoring module is set to the continuous monitoring mode. When the communication mode between the monitoring module and the monitoring device is the WA/ITS mode, the monitoring module is away from the monitoring device, which indicates that the patient may be outside the ward and is in a good physical condition. The working mode of the monitoring module may be set to the discontinuous monitoring mode.

Optionally, the monitoring module further comprises a storage unit configured to store physiological data of the patient that is obtained within a preset time period; and the status parameter of the device comprises a total capacity of storage space of the monitoring module.

Optionally, in terms of the obtaining a parameter, and setting a working mode of the monitoring module according to the obtained parameter, the processor is specifically configured to: obtain the total capacity of storage space from the storage unit; determine a first continuous mode working time and a first discontinuous mode working time that can be supported by the total capacity of storage space, the sum of an amount of data obtained during the first continuous mode working time and an amount of data obtained during the first discontinuous mode working time being equal to the total capacity of storage space; obtain a continuous mode working time T1 that has been supported, and set, when the first value comparison result is that T1 is greater than or equal to the first continuous mode working time, the working mode of the monitoring module to the discontinuous monitoring mode; or set, when the first value comparison result is that T1 is less than the first continuous mode working time, the working mode of the monitoring module to the continuous monitoring mode.

Specifically, the monitoring module is configured to obtain a parameter, and the parameter is transferred to the monitoring device for analysis and display. In this process, data needs to be stored in the monitoring module for a period of time. With the limited storage space, in order to ensure a data storage time, it is necessary to control data obtaining. An amount of data stored in the continuous monitoring mode is far greater than that of data stored in the discontinuous monitoring mode. In the case of the limited storage space, it is necessary to consider how to optimize the time allocation of the continuous monitoring mode and the discontinuous monitoring mode, so that on the premise of rigorous patient monitoring, the amount of monitoring-related data does not exceed the total capacity of storage space.

Figure 13:
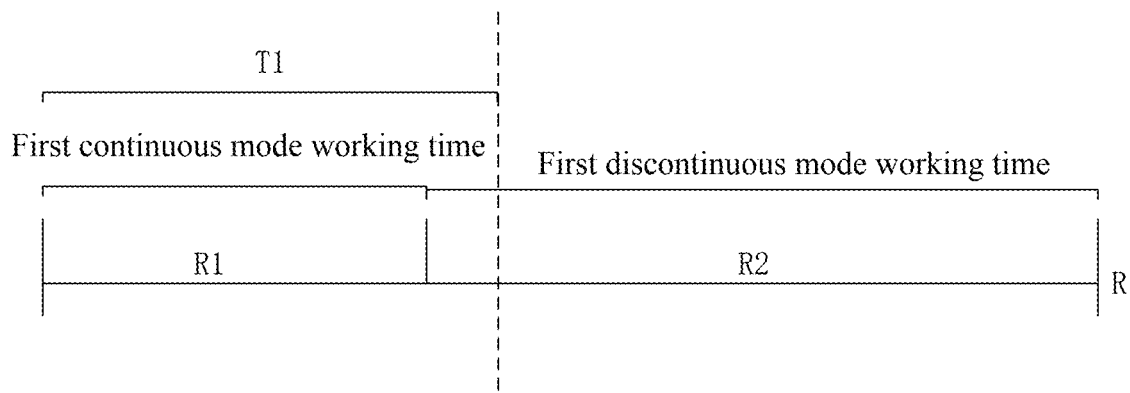
FIG. 13 is a schematic diagram of a correspondence between a spatial storage amount and a monitoring mode according to an embodiment of the present application.

Referring to FIG. 13, FIG. 13 is a schematic diagram of a correspondence between a spatial storage amount and a monitoring mode according to an embodiment of the present application. As shown in FIG. 13, during the first continuous mode working time, the monitoring module is in the continuous monitoring mode, and storage space occupied by an amount of obtained data is R1; during the first discontinuous mode working time, the monitoring module is in the discontinuous monitoring mode, and storage space occupied by an amount of obtained data is R2, the sum of R1 and R2 being the total space capacity R. The continuous mode working time T1 that has been currently supported by the patient status monitoring system is obtained. When T1≥the first continuous mode working time, it indicates that the storage space can no longer support the continuous monitoring mode, and the discontinuous monitoring mode needs to be used. Therefore, the working mode of the monitoring module is set to the discontinuous monitoring mode. Similarly, when T1<the first continuous mode working time, it indicates that the storage space can still support the continuous monitoring mode. Then, the working mode of the monitoring module is set to the continuous monitoring mode.

Optionally, the monitoring device or the monitoring module further comprises a power supply unit, and the status parameter of the device comprises a total available electric quantity of the monitoring device or the monitoring module.

Optionally, in terms of the obtaining a parameter, and setting a working mode of the monitoring module according to the obtained parameter, the processor is specifically configured to: obtain the total available electric quantity of the corresponding device from the monitoring device or the monitoring module; determine a second continuous mode working time and a second discontinuous mode working time that can be supported by the total available electric quantity, the sum of an electric quantity consumed during the second continuous mode working time and an electric quantity consumed during the second discontinuous mode working time being equal to the total available electric quantity; obtain a continuous mode working time T2 that has been supported, and set, when the second value comparison result is that T2 is greater than or equal to the second continuous mode working time, the working mode of the monitoring module to the discontinuous monitoring mode; or set, when the second value comparison result is that T2 is less than the second continuous mode working time, the working mode of the monitoring module to the continuous monitoring mode.

Specifically, during the monitoring of the patient, there may be cases where one of the monitoring device or the monitoring module is powered by a battery, or both are powered by a battery, or conservation of electricity is considered. The continuous monitoring mode and the discontinuous monitoring mode have different power consumption, and the power consumption of the continuous monitoring mode is far greater than that of the discontinuous monitoring mode. In the case of limited electric power, to make the limited electric power meet a specific endurance time, it is necessary to consider how to optimize the time allocation of the continuous monitoring mode and the discontinuous monitoring mode. When the total available electric quantity is obtained, in order to ensure that both the monitoring module and the monitoring device can work properly, a smaller available electric quantity between the two devices should be obtained and used as the total available electric quantity.

Figure 14:
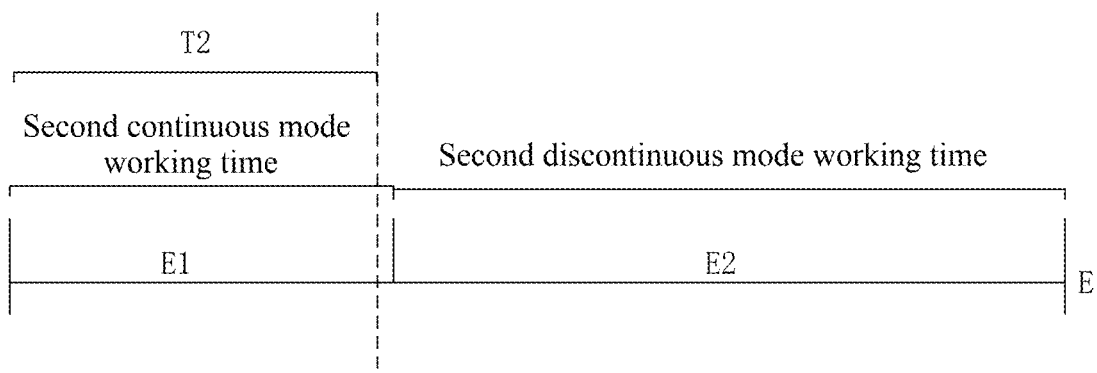
FIG. 14 is a schematic diagram of a correspondence between battery power and a monitoring mode according to an embodiment of the present application.

Referring to FIG. 14. FIG. 14 is a schematic diagram of a correspondence between battery power and a monitoring mode according to an embodiment of the present application. As shown in FIG. 14, during the second continuous mode working time, the monitoring module is in the continuous monitoring mode, and an electric quantity consumed is E1; during the second discontinuous mode working time, the monitoring module is in the discontinuous monitoring mode, and an electric quantity consumed is E2, the sum of E1 and E2 being the total battery power E. The continuous mode working time T2 that has been currently supported by the patient status monitoring system is obtained. When T2≥the second continuous mode working time, it indicates that the battery power can no longer support the continuous monitoring mode, and the discontinuous monitoring mode needs to be used. Therefore, the working mode of the monitoring module is set to the discontinuous monitoring mode. Similarly, when T2<the second continuous mode working time, it indicates that the battery power can still support the continuous monitoring mode. Then, the working mode of the monitoring device may be set to the continuous monitoring mode.

Optionally, the monitoring module further comprises: a parameter obtaining module configured to obtain a monitored parameter of the patient; a classification module connected to the parameter obtaining module and configured to determine a parameter category to which the monitored parameter of the patient belongs, wherein the parameter category comprises a continuous measurement parameter type and a discontinuous measurement parameter type; and the processor connected to the classification module and configured to determine the working mode of the monitoring module according to the parameter category.

The continuous measurement parameter type comprises an electrocardiogram (ECG), blood pressure (NIBP), and/or a motion parameter; the discontinuous measurement parameter type comprises respiration (RESP), blood oxygen (SPO2), and/or body temperature (TEMP); and in terms of the obtaining a parameter, and setting a working mode of the monitoring module according to the obtained parameter, the processor is specifically configured to: set, when it is determined that the monitored parameter of the patient belongs to the continuous measurement parameter type, the working mode of the monitoring module to the continuous monitoring mode; or set, when it is determined that the monitored parameter of the patient belongs to the discontinuous measurement parameter type, the working mode of the monitoring module to the discontinuous monitoring mode.

Specifically, the continuous measurement parameter type and the discontinuous measurement parameter type are set, and the working mode of the monitoring module is determined according to the parameter category. In such a manner, the working mode of the monitoring module can be determined more efficiently and quickly. Parameters such as the ECG, NIBP, or motion parameter are important parameters, which are of great reference to the physical condition of the patient and need to be obtained in real time to rigorously monitor the physical condition of the patient.

These parameters are set as continuous measurement parameters. Parameters such as the RESP, SPO2, or TEMP are of little reference to the physical condition of the patient, and therefore these parameters may be obtained in a sporadic measurement manner, for example, obtained at specific intervals, wherein the interval may be 2 min, 5 min, etc. These parameters are set as discontinuous measurement parameters. When the continuous measurement parameters are obtained, the working mode of the monitoring module is set to the continuous monitoring mode, and when the discontinuous measurement parameters are obtained, the working mode of the monitoring module is set to the discontinuous monitoring mode.

Optionally, the processor is further configured to obtain signal strength of the monitoring module, and determine a communication mode of the monitoring module according to the signal strength.

Because the communication mode of the monitoring module can be used to determine the working mode of the monitoring module, it is also of great importance to determine the communication mode of the monitoring module. The working mode of the monitoring module is determined based on the signal strength of the monitoring module, which can ensure that the monitoring module maintains good communication and reduce data delay or data loss caused by a network with poor quality.

Optionally, in terms of the obtaining signal strength of the monitoring module, and determining a communication mode of the monitoring module according to the signal strength, the processor is specifically configured to: obtain the signal strength of the monitoring module, wherein the signal strength comprises WMTS signal strength and Wi-Fi signal strength; and determine, when the WMTS signal strength is greater than or equal to a first preset threshold, that the communication mode of the monitoring module is a WMTS mode; or determine, when the WMTS signal strength is less than the first preset threshold, that the communication mode of the monitoring module is a Wi-Fi mode.

Specifically, it can be learned from the foregoing embodiment that the monitoring module can switch between the WMTS communication mode and the Wi-Fi communication mode depending on whether the patient is in the ward or outside the ward. In fact, the reason is that the monitoring device is located at the bedside. When the patient is in the ward, the WMTS signal strength is high, while the Wi-Fi signal strength is low. When the patient is outside the ward, the WMTS signal strength is low, while the Wi-Fi signal strength is high. Priority is given to the WMTS mode, and it is determined, when the WMTS signal strength is greater than or equal to a first preset threshold, that the communication mode of the monitoring module is a WMTS mode; or it is determined, when the WMTS signal strength is less than the first preset threshold, that the communication mode of the monitoring module is a Wi-Fi mode. In this way, the method for determining the communication mode only based on the signal strength can further eliminate interference caused by being in or outside the ward.

Optionally, the processor is further configured to: when it is determined that the communication mode of the monitoring module is the WMTS mode, obtain a first packet loss rate of the monitoring module and determine whether the first packet loss rate is less than a second preset threshold, and determine the communication mode of the monitoring module according to a determination result.

Optionally, in terms of the determining the communication mode of the monitoring module according to a determination result, the processor is further configured to: when the first packet loss rate is less than the second preset threshold, maintain the WMTS mode; or when the first packet loss rate is greater than or equal to the second preset threshold, switch the communication mode of the monitoring module to the Wi-Fi mode.

Specifically, the communication mode of the monitoring module is not only related to the signal strength, but is also related to the packet loss rate. When the monitoring module is in the WMTS mode, it is required to further determine the packet loss rate corresponding to the current communication mode. If the packet loss rate is too high, it indicates that the communication quality is not good, and the communication mode of the monitoring module needs to be switched to the Wi-Fi mode. If the packet loss rate is less than the second preset threshold, it indicates that the current communication quality is good, and the WMTS mode is maintained. The packet loss rate is a rate value, which may be set to 0.05%, 0.02%, 0.01%, etc.

Optionally, after the obtaining a parameter, and setting a working mode of the monitoring module according to the obtained parameter, the processor is further configured to set a communication mode of the monitoring module according to the working mode of the monitoring module.

Optionally, the processor being further configured to set a communication mode of the monitoring module according to the working mode of the monitoring module comprises: when the working mode of the monitoring module is the discontinuous monitoring mode, setting the communication mode of the monitoring module to a Wi-Fi mode; or when the working mode of the monitoring module is the continuous monitoring mode, setting the communication mode of the monitoring module to a WMTS mode.

Specifically, the working mode of the monitoring module is closely related to the communication mode, and the working mode can be determined based on the communication mode of the monitoring module. Conversely, the communication mode can also be determined based on the working mode of the monitoring module. For example, when the working mode of the monitoring module is the continuous working mode, it indicates that good communication quality and a high-reliability network are required at this time, such that the efficiency and accuracy of obtaining the body parameters of the patient can be higher. In this case, the WMTS mode is used. When the working mode of the monitoring module is the discontinuous working mode, there are low requirements for communication quality and network reliability, and then the Wi-Fi mode may be used.

Optionally, the monitoring module comprises a first monitoring sub-module and a second monitoring sub-module, and the continuous monitoring mode specifically comprises: continuously obtaining, by the first monitoring sub-module, a first type of parameter in real time, wherein the first type of parameter comprises an electrocardiogram (ECG), respiration (RESP), blood oxygen (SPO2), and/or body temperature (TEMP); continuously obtaining, by the second monitoring sub-module, a second type of parameter in real time, wherein the second type of parameter comprises blood pressure (NIBP) and/or a motion signal; sending, by the second monitoring sub-module, the second type of parameter to the first monitoring sub-module in real time; and continuously sending, by the first monitoring sub-module, the first type of parameter and the second type of parameter to a first monitoring device in real time, and updating, by the first monitoring device, a parameter waveform and/or parameter value in an interface in real time.

Specifically, the continuous monitoring mode means obtaining parameters continuously and uninterruptedly, and monitoring the physical condition of the patient in real time. This monitoring mode deals with the situation where the patient is in a poor physical condition and requires rigorous monitoring. For the structure of the monitoring module shown in FIG. 4, the first monitoring sub-module may be an ECG-POD, which can obtain ECG, RESP, SPO2, TEMP, and other body parameters continuously and in real time, and the second monitoring sub-module may be an NIBP-POD, which can collect body parameters such as NIBP and a motion signal continuously and in real time. Because the ECG-POD is the main control module and is responsible for external communication, the NIBP-POD sends the collected body parameters to the ECG-POD, and the ECG-POD communicates wirelessly to send the body parameters collected by itself and the received body parameters collected by the NIBP-POD to the monitoring device together.

Optionally, the monitoring module comprises a third monitoring sub-module and a fourth monitoring sub-module, and the discontinuous monitoring mode specifically comprises: continuously obtaining, by the third monitoring module, a third type of parameter in real time, and simultaneously obtaining a fourth type of body parameter at preset frequency, wherein the third type of parameter comprises the electrocardiogram (ECG), the fourth type of body parameter comprises the respiration (RESP), the blood oxygen (SPO2), and/or the body temperature (TEMP), and continuously obtaining, by the fourth monitoring module, a fifth type of body parameter in real time, wherein the fifth type of body parameter comprises the blood pressure (NIBP) and/or the motion signal; sending, by the fourth monitoring module, the fifth type of body parameter to the first monitoring sub-module in real time; and sending, by the first monitoring sub-module, body parameters consisting of the third type of body parameter, the fourth type of body parameter, and the fifth type of body parameter to a central station in real time, forwarding, by the central station, the body parameters to a second monitoring device, and updating, by the second monitoring device, a parameter waveform and/or parameter value in an interface, wherein the preset frequency is greater than or equal to zero.

Specifically, in an embodiment, when the preset frequency refers to a monitoring mode in which parameters are collected for fixed duration at fixed time intervals, and then the collected parameters are sent to the monitoring device in real time. For example, if the fixed time interval is 2 minutes and the fixed duration is 15 seconds, the monitoring module may collect all body parameters for 15 seconds every 2 minutes and send the collected body parameters to the monitoring device. Alternatively, some of the body parameters may be collected for 15 seconds every 2 minutes, and the remaining body parameters are obtained continuously and uninterruptedly. All the body parameters are collected and then sent to the monitoring device in real time and synchronously. The monitoring device analyzes and presents the body parameters, including text presentation or image presentation. Specifically, the monitoring device updates the parameter waveform or parameter value in the interface, or updates both at the same time. Alternatively, when the patient is in upright motion independently, the measurement of the respiration (RESP), blood oxygen (SPO2), and/or body temperature (TEMP) may be disabled, and alarms related to the respiration (RESP), blood oxygen (SPO2), and/or body temperature (TEMP) may be further suppressed or canceled. In this case, the preset frequency is zero.

It can be learned that in this embodiment of the present application, the working mode of the monitoring module is set based on the parameters such as the communication mode of the monitoring module, the condition of the patient, the duration of the motion signal of the patient, the storage space capacity, or the available electric quantity. In this process, by switching the monitoring mode, in the process of monitoring the patient, it can not only achieve the rigorous monitoring of the physical condition of the user, but also reduce the processing of redundant data, which improves the efficiency and quality of monitoring.

Figure 15:
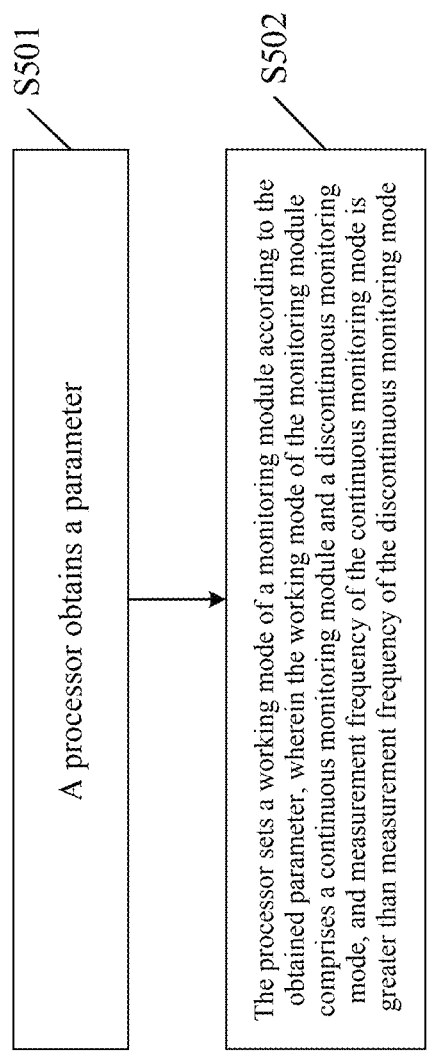
FIG. 15 is a schematic flowchart of a patient status monitoring method according to an embodiment of the present application.

Referring to FIG. 15, FIG. 15 is a schematic flowchart of a patient status monitoring method according to an embodiment of the present application. The patient status monitoring method is applied to a patient status monitoring system comprising a monitoring device and a monitoring module communicatively connected to the monitoring device, the monitoring module being worn on the body of a patient and comprises a processor. As shown in FIG. 15, the patient status monitoring method comprises the steps as follows.

S501: The processor obtains a parameter.

S502: A working mode of the monitoring module is set according to the obtained parameter. The working mode of the monitoring module comprises a continuous monitoring module and a discontinuous monitoring mode. Frequency of the continuous monitoring mode is greater than frequency of the discontinuous monitoring mode, wherein the frequency comprises measurement frequency of the monitoring module and frequency of data transmission between the monitoring device and the monitoring module, and the frequency of the continuous monitoring mode being greater than the frequency of the discontinuous monitoring mode comprises at least one of the following two conditions: measurement frequency of the monitoring module in the continuous monitoring mode is greater than measurement frequency of the monitoring module in the discontinuous monitoring mode, and frequency of data transmission in the continuous monitoring mode is greater than frequency of data transmission in the discontinuous monitoring mode.

In a possible embodiment, the monitoring module further comprises: a parameter measurement unit configured to detect a physiological parameter of the patient, wherein the monitored parameter of the patient comprises the physiological parameter.

In a possible embodiment, the obtaining a parameter, and setting a working mode of the monitoring module according to the obtained parameter comprises:

obtaining the physiological parameter of the patient from the parameter measurement unit, wherein the physiological parameter comprises an electrocardiogram (ECG), blood oxygen (SPO2), body temperature (TEMP), and/or blood pressure (NIBP);

determining a condition of the patient according to the physiological parameter, wherein the condition comprises good or critical; and setting, when the condition is good, the working mode of the monitoring module to the continuous monitoring mode; or setting, when the condition is critical, the working mode of the monitoring module to the discontinuous monitoring mode.

In a possible embodiment, the monitoring module further comprises: a motion sensor configured to detect a motion parameter of the patient, wherein the monitored parameter of the patient comprises the motion parameter.

In a possible embodiment, the obtaining a parameter, and setting a working mode of the monitoring module according to the obtained parameter comprises:
- obtaining the motion parameter of the patient from the motion sensor, and obtaining duration of a motion signal of the patient according to the motion parameter;
- setting, when the duration of the motion signal is greater than or equal to the first preset duration, the working mode of the monitoring module to the discontinuous monitoring mode; or
- setting, when the duration of the motion signal is less than the first preset duration, the working mode of the monitoring module to the continuous monitoring mode.

In a possible embodiment, the motion sensor is a three-axis accelerometer, and the motion parameter is acceleration; and before the duration of the motion signal of the patient is obtained, the method further comprises: determining that the patient is in an outdoor upright motion state, which specifically comprises:
- determining that a communication mode of the monitoring module is a Wi-Fi mode;
- determining, according to the acceleration, that a range of motion of the patient is greater than a first preset range;
- determining that an included angle between the direction of the acceleration of the accelerometer and the positive direction of the Z-axis is less than a first preset angle, the positive direction of the Z-axis being a downward direction perpendicular to a horizontal plane; and
- determining that the patient is in the outdoor upright motion state.

In a possible embodiment, the status parameter of the device comprises a distance between the monitoring device and the monitoring module.

In a possible embodiment, the obtaining a parameter from the monitoring device and/or the monitoring module, and setting a working mode of the monitoring module according to the obtained parameter comprises:
- obtaining a distance between the monitoring device and the monitoring module from the monitoring device and/or the monitoring module, wherein the distance may be determined according to the communication mode of the monitoring module: when the communication mode is a wireless medical telemetry service (WMTS) mode, the monitoring device is close to the monitoring module; and when the communication mode is a wireless fidelity (Wi-Fi) mode, the monitoring device is away from the monitoring module; and
- setting, if it is determined that the monitoring device is away from the monitoring module, the working mode of the monitoring module to the discontinuous monitoring mode; or
- setting, if it is determined that the monitoring device is close to the monitoring module, the working mode of the monitoring module to the continuous monitoring mode.

In a possible embodiment, the obtaining a parameter from the monitoring device and/or the monitoring module, and setting a working mode of the monitoring module according to the obtained parameter comprises:
- obtaining communication signal strength and a packet loss rate between the monitoring device and the monitoring module;
- determining a distance between the monitoring device and the monitoring module according to the communication signal strength and the packet loss rate; and
- when the communication signal strength is greater than a first signal threshold and the packet loss rate is less than a first preset threshold, determining that the monitoring device is close to the monitoring module, and setting the working mode of the monitoring module to the continuous monitoring mode; or
- when the communication signal strength is less than the first signal threshold and the packet loss rate is greater than the first preset threshold, determining that the monitoring device is away from the monitoring module, and setting the working mode of the monitoring module to the discontinuous monitoring mode.

In a possible embodiment, the status parameter of the device comprises a total capacity of storage space of the monitoring device and/or the monitoring module, and the obtaining a parameter from the monitoring device and/or the monitoring module, and setting a working mode of the monitoring module according to the obtained parameter comprises:
- obtaining the total capacity of storage space of the monitoring device and/or the monitoring module from the monitoring device and/or the monitoring module;
- determining a first continuous mode working time and a first discontinuous mode working time that can be supported by the total capacity of storage space, the sum of an amount of data obtained during the first continuous mode working time and an amount of data obtained during the first discontinuous mode working time being equal to the total capacity of storage space;
- obtaining a continuous mode working time T1 that has been supported, and setting, when the first value comparison result is that T1 is greater than or equal to the first continuous mode working time, the working mode of the monitoring module to the discontinuous monitoring mode; or
- setting, when the first value comparison result is that T1 is less than the first continuous mode working time, the working mode of the monitoring module to the continuous monitoring mode.

In a possible embodiment, the status parameter of the device comprises a total available electric quantity of the monitoring device or the monitoring module, and the obtaining a parameter from the monitoring device and/or the monitoring module, and setting a working mode of the monitoring module according to the obtained parameter comprises:
- obtaining the total available electric quantity of the corresponding device from the monitoring device or the monitoring module;
- determining a second continuous mode working time and a second discontinuous mode working time that can be supported by the total available electric quantity, the sum of an electric quantity consumed during the second continuous mode working time and an electric quantity consumed during the second discontinuous mode working time being equal to the total available electric quantity;
- obtaining a continuous mode working time T2 that has been supported, and setting, when the second value comparison result is that T2 is not less than the second continuous mode working time, the first monitoring mode to the discontinuous monitoring mode; or
- if the second value comparison result is that T2 is less than the second continuous mode working time, determining whether the first monitoring mode is a continuous monitoring mode, and if the first monitoring mode is not the continuous monitoring mode, switching the working mode of the monitoring module.

In a possible embodiment, the monitoring module further comprises: a parameter obtaining module configured to obtain a monitored parameter of the patient; a classification module connected to the parameter obtaining module and configured to determine a parameter category to which the monitored parameter of the patient belongs, wherein the parameter category comprises a continuous measurement parameter type and a discontinuous measurement parameter type; and the processor connected to the classification module and configured to determine the working mode of the monitoring module according to the parameter category.

In a possible embodiment, the continuous measurement parameter type comprises an electrocardiogram (ECG), blood pressure (NIBP), and/or a motion signal; the discontinuous measurement parameter type comprises respiration (RESP), blood oxygen (SPO2), and/or body temperature (TEMP); and the setting a working mode of the monitoring module according to the obtained parameter comprises:
    setting, when it is determined that the monitored parameter of the patient belongs to the continuous measurement parameter type, the working mode of the monitoring module to the continuous monitoring mode; or
    setting, when it is determined that the monitored parameter of the patient belongs to the discontinuous measurement parameter type, the working mode of the monitoring module to the discontinuous monitoring mode.

In a possible embodiment, before the obtaining a distance between the monitoring device and the monitoring module from the monitoring device and/or the monitoring module, the method further comprises determining the communication mode of the monitoring module, which specifically comprises:
    obtaining the signal strength of the monitoring module, wherein the signal strength comprises WMTS signal strength and Wi-Fi signal strength; and
    detecting whether the WMTS signal strength is greater than a first preset threshold, and if the WMTS signal strength is greater than the first preset threshold, determining that the wireless communication mode of the monitoring module is a WMTS mode; or
    if the WMTS signal strength is not greater than the first preset threshold, detecting whether the Wi-Fi signal strength is greater than a second preset threshold, and if the Wi-Fi signal strength is greater than the second preset threshold, determining that the wireless communication mode of the monitoring module is a Wi-Fi mode.

In a possible embodiment, after it is determined that the wireless communication mode of the monitoring module is the WMTS mode, the method further comprises:
    obtaining a first packet loss rate of the monitoring module and determining whether the first packet loss rate is less than a second preset threshold, and determining the wireless communication mode of the monitoring module according to a determination result.

In a possible embodiment, the determining the wireless communication mode of the monitoring module according to a determination result comprises:
    when the first packet loss rate is less than the second preset threshold, maintaining the WMTS mode; or
    when the first packet loss rate is greater than or equal to the second preset threshold, switching the wireless communication mode of the monitoring module to the Wi-Fi mode.

In a possible embodiment, after the obtaining a parameter, and setting a working mode of the monitoring module according to the obtained parameter, the method further comprises setting a communication mode of the monitoring module according to the working mode of the monitoring module.

In a possible embodiment, the setting a communication mode of the monitoring module according to the working mode of the monitoring module comprises:
    when the working mode of the monitoring module is the discontinuous monitoring mode, setting the communication mode of the monitoring module to a Wi-Fi mode; or
    when the working mode of the monitoring module is the continuous monitoring mode, setting the communication mode of the monitoring module to a WMTS mode.

It should be noted herein that for the specific description of the method corresponding to the above steps, reference may be made to the related descriptions of the above embodiments shown in FIGS. 1 to 13, and details are not repeated herein.

An embodiment of the present application further provides a computer storage medium, wherein the computer storage medium may store a program, and the program, when executed, comprises some or all of the steps of any obstacle avoidance method recorded in the above method embodiments.

The embodiments of the present application have been described above in detail, specific examples are used herein to explain the principles and implementations of the present application, and the description of the embodiments is only intended to facilitate understanding of the method of the present application and the core idea thereof. Moreover, for those skilled in the art, there can be modifications in the specific implementation and application scope based on the idea of the present application, and to sum up, the content of this specification should not be construed as limiting the present application.

The invention claimed is:

1. A method for monitoring patient status, applied to a patient status monitoring system comprising a monitoring device and a monitoring module communicatively connected to the monitoring device, the monitoring module being wearable on a body of a patient and comprising a processor, wherein the method comprises:
    obtaining, by the processor, a parameter, and
    setting a working mode of the monitoring module according to the obtained parameter, wherein the working mode of the monitoring module comprises at least one of a continuous monitoring module or a discontinuous monitoring mode;
    wherein:
        when the monitoring module is in the continuous monitoring mode, the monitoring device is a ward-level monitoring device, and the monitoring module communicates with the ward-level monitoring device; and
        when the monitoring module is in the discontinuous monitoring mode, the monitoring device is a department-level monitoring device, and the monitoring module communicates with the department-level monitoring device.

2. The method of claim 1, wherein the parameter comprises at least one of a monitored parameter of the patient or a status parameter of a device.

3. The method of claim 1, wherein a frequency of the continuous monitoring mode is greater than a frequency of the discontinuous monitoring mode, wherein the frequency of the continuous monitoring mode or the frequency of the discontinuous monitoring mode comprises a measurement frequency of the monitoring module or a frequency of data transmission between the monitoring device and the monitoring module, and wherein a measurement frequency of the monitoring module in the continuous monitoring mode is greater than a measurement frequency of the monitoring module in the discontinuous monitoring mode, or a frequency of data transmission in the continuous monitoring mode is greater than a frequency of data transmission in the discontinuous monitoring mode.

4. The method of claim 1, wherein setting a working mode of the monitoring module according to the obtained parameter comprises:
   obtaining a communication mode between the monitoring device and the monitoring module, and
   switching the working mode of the monitoring module between the continuous monitoring mode and the discontinuous monitoring mode according to a change of the communication mode.

5. The method of claim 2, wherein the parameter comprises the monitored parameter of the patient and the monitored parameter of the patient comprises a physiological parameter; and the monitoring module comprises: a parameter measurement unit configured to detect the physiological parameter of the patient, wherein obtaining a parameter, and setting a working mode of the monitoring module according to the obtained parameter comprises:
   obtaining the physiological parameter of the patient from the parameter measurement unit, wherein the physiological parameter comprises at least one of electrocardiogram (ECG), blood oxygen (SPO2), body temperature (TEMP), or blood pressure (NIBP);
   determining a condition of the patient according to the physiological parameter, wherein the condition comprises good or critical; and
   when the condition is good, setting the working mode of the monitoring module to the discontinuous monitoring mode; or
   when the condition is critical, setting the working mode of the monitoring module to the continuous monitoring mode.

6. The method of claim 2, wherein the parameter comprises the monitored parameter of the patient and the monitored parameter of the patient comprises a motion parameter of the patient; and the monitoring module comprises: a motion sensor configured to detect the motion parameter of the patient, wherein obtaining a parameter, and setting a working mode of the monitoring module according to the obtained parameter comprises:
   obtaining the motion parameter of the patient from the motion sensor, and obtaining a duration of a motion signal of the patient according to the motion parameter;
   making a value comparison between the duration of the motion signal and a first preset duration, to obtain a comparison result; and
   when the comparison result indicates that the duration of the motion signal is greater than or equal to the first preset duration, setting the working mode of the monitoring module to the discontinuous monitoring mode; or
   when the comparison result indicates that the duration of the motion signal is less than the first preset duration, setting the working mode of the monitoring module to the continuous monitoring mode.

7. The method of claim 1, wherein the monitoring module comprises a three-axis accelerometer configured to detect a motion parameter of the patient, and the motion parameter is acceleration; the method further comprises: determining that the patient is in an outdoor upright motion state, which comprises:
   determining that a communication mode of the monitoring module is a Wi-Fi mode;
   determining, according to the acceleration, that a range of motion of the patient is greater than a first preset range;
   determining that an included angle between a direction of the acceleration of the accelerometer and a positive direction of Z-axis is less than a first preset angle, the positive direction of Z-axis being a downward direction perpendicular to a horizontal plane; and
   determining that the patient is in the outdoor upright motion state.

8. The method of claim 2, wherein the parameter comprises the status parameter of the device and the status parameter of the device comprises a communication mode, wherein the communication mode comprises a wireless medical telemetry service (WMTS) mode or a Wi-Fi mode, wherein obtaining a parameter from the monitoring device or the monitoring module, and setting a working mode of the monitoring module according to the obtained parameter comprises:
   obtaining a communication mode between the monitoring device and the monitoring module from the monitoring device or the monitoring module, and, when the communication mode is the wireless medical telemetry service (WMTS) mode, setting the working mode of the monitoring module to the continuous monitoring mode; or
   when the communication mode is the Wi-Fi mode, setting the working mode of the monitoring module to the discontinuous monitoring mode.

9. The method of claim 2, wherein the parameter comprises the status parameter of the device and the status parameter of the device comprises: communication features of the monitoring device and the monitoring module, wherein the communication features comprise communication signal strength and a packet loss rate, wherein obtaining a parameter from the monitoring device or the monitoring module, and setting a working mode of the monitoring module according to the obtained parameter comprises:
   obtaining communication signal strength and a packet loss rate between the monitoring device and the monitoring module; and
   when the communication signal strength is greater than a first signal threshold and the packet loss rate is less than a first preset threshold, setting the working mode of the monitoring module to the continuous monitoring mode; or
   when the communication signal strength is less than a first signal threshold and the packet loss rate is greater than a first preset threshold, setting the working mode of the monitoring module to the discontinuous monitoring mode.

10. The method of claim 2, wherein the parameter comprises the status parameter of the device and the system comprises a storage unit configured to store physiological data of the patient that is obtained within a preset time period; and the status parameter of the device comprises a total capacity of storage space of the system, wherein obtaining a parameter from the monitoring device or the monitoring module, and setting a working mode of the monitoring module according to the obtained parameter comprises:

obtaining a total capacity of storage space of the monitoring device or the monitoring module from the monitoring device or the monitoring module;
determining a first continuous mode working time and a first discontinuous mode working time that are supported by the total capacity of storage space, a sum of an amount of data obtained during the first continuous mode working time and an amount of data obtained during the first discontinuous mode working time being equal to the total capacity of storage space;
obtaining a continuous mode working time T1 that has been supported by the total capacity of storage space, and
wherein:
when T1 is greater than or equal to the first continuous mode working time, setting the working mode of the monitoring module to the discontinuous monitoring mode; or
when T1 is less than the first continuous mode working time setting the working mode of the monitoring module to the continuous monitoring mode.

11. The method of claim 2, wherein the parameter comprises the status parameter of the device and the monitoring device or the monitoring module comprises a power supply unit, and the status parameter of the device comprises a total available electric quantity of the monitoring device or the monitoring module, wherein obtaining a parameter from the monitoring device or the monitoring module, and setting a working mode of the monitoring module according to the obtained parameter comprises:
obtaining a total available electric quantity of the monitoring device or the monitoring module from the monitoring device or the monitoring module;
determining a second continuous mode working time and a second discontinuous mode working time that are supported by the total available electric quantity, a sum of an electric quantity consumed during the second continuous mode working time and an electric quantity consumed during the second discontinuous mode working time being equal to the total available electric quantity;
obtaining a continuous mode working time T2 that has been supported by the total available electric quantity, and
wherein:
when T2 is not less than the second continuous mode working time, setting the working mode of the monitoring module to the discontinuous monitoring mode; or
when T2 is less than the second continuous mode working time, determining whether the working mode of the monitoring module is a continuous monitoring mode, and if the working mode of the monitoring module is not the continuous monitoring mode, switching the working mode of the monitoring module to continuous monitoring mode.

12. The method of claim 1, further comprising: obtaining a monitored parameter of the patient; determining a parameter category to which the monitored parameter of the patient belongs, wherein the parameter category comprises a continuous measurement parameter type and a discontinuous measurement parameter type; and determining the working mode of the monitoring module according to the parameter category.

13. The method of claim 12, wherein the continuous measurement parameter type comprises an electrocardiogram (ECG), a blood pressure (NIBP), or a motion signal; the discontinuous measurement parameter type comprises respiration (RESP), blood oxygen (SPO2), or body temperature (TEMP); and
setting a working mode of the monitoring module according to the obtained parameter comprises:
when it is determined that the monitored parameter of the patient belongs to the continuous measurement parameter type, setting the working mode of the monitoring module to the continuous monitoring mode; or
when it is determined that the monitored parameter of the patient belongs to the discontinuous measurement parameter type, setting the working mode of the monitoring module to the discontinuous monitoring mode.

14. The method of claim 1, wherein the method further comprises:
obtaining signal strength of the monitoring module, wherein the signal strength comprises wireless medical telemetry service (WMTS) signal strength and Wi-Fi signal strength; and
detecting whether the WMTS signal strength is greater than a first preset threshold of signal strength, and wherein:
when the WMTS signal strength is greater than the first preset threshold of signal strength, determining that a wireless communication mode of the monitoring module is a WMTS mode; or
when the WMTS signal strength is not greater than the first preset threshold of signal strength, detecting whether the Wi-Fi signal strength is greater than a second preset threshold of signal strength, and if the Wi-Fi signal strength is greater than the second preset threshold of signal strength, determining that the wireless communication mode of the monitoring module is a Wi-Fi mode.

15. The method of claim 14, wherein, after it is determined that the wireless communication mode of the monitoring module is the WMTS mode, the method further comprises:
obtaining a first packet loss rate of the monitoring module and determining whether the first packet loss rate is less than a second preset threshold of packet loss rate, and wherein:
when the first packet loss rate is less than the second preset threshold of packet loss rate, maintaining the WMTS mode; or
when the first packet loss rate is greater than or equal to the second preset threshold of packet loss rate, switching the wireless communication mode of the monitoring module to the Wi-Fi mode.

16. The method of claim 1, wherein, after the obtaining a parameter, and setting a working mode of the monitoring module according to the obtained parameter, the method further comprises:
when the working mode of the monitoring module is the discontinuous monitoring mode, setting a communication mode of the monitoring module to a Wi-Fi mode; or
when the working mode of the monitoring module is the continuous monitoring mode, setting a communication mode of the monitoring module to a wireless medical telemetry service (WMTS) mode.

17. The method of claim 1, wherein the monitoring module comprises a first monitoring sub-module and a second monitoring sub-module, and when the working mode of monitoring module is the continuous monitoring mode, the method further comprises:

continuously obtaining, by the first monitoring sub-module, a first type of physical parameter in real time, wherein the first type of body parameter comprises electrocardiogram (ECG), respiration (RESP), blood oxygen (SPO2), or body temperature (TEMP);

continuously obtaining, by the second monitoring sub-module, a second type of body parameter in real time, wherein the second type of body parameter comprises a blood pressure (NIBP) or a motion signal;

sending, by the second monitoring sub-module, the second type of body parameter to the first monitoring sub-module in real time; and continuously sending, by the first monitoring submodule, the first type of body parameter and the second type of body parameter to the monitoring device in real time.

18. The method of claim 1, wherein the monitoring module comprises a third monitoring submodule and a fourth monitoring submodule, and when the working mode of monitoring module is the continuous monitoring mode, the method further comprises:

continuously obtaining, by the third monitoring sub-module, a third type of body parameter in real time, and simultaneously obtaining a fourth type of body parameter at a preset frequency, wherein the third type of body parameter comprises electrocardiogram (ECG), the fourth type of body parameter comprises respiration (RESP), blood oxygen (SPO2), or body temperature (TEMP), and a preset frequency is greater than zero;

continuously obtaining, by the fourth monitoring sub-module, a fifth type of body parameter in real time, wherein the fifth type of body parameter comprises a blood pressure (NIBP) or a motion signal;

sending, by the fourth monitoring sub-module, the fifth type of body parameter to the third monitoring sub-module in real time; and sending, by the third monitoring sub-module, the third type of body parameter, the fourth type of body parameter, and the fifth type of body parameter to the monitoring device in real time.

19. A patient status monitoring system, comprising:

a monitoring device; and a monitoring module communicatively connected to the monitoring device, wherein the monitoring module is worn on the body of a patient and comprises: a processor configured to obtain a parameter, and set a working mode of the monitoring module according to the obtained parameter, wherein the working mode of the monitoring module comprises at least one of a continuous monitoring module or a discontinuous monitoring mode;

wherein:

when the monitoring module is in the continuous monitoring mode, the monitoring device is a ward-level monitoring device, and the monitoring module communicates with the ward-level monitoring device; and when the monitoring module is in the discontinuous monitoring mode, the monitoring device is a department-level monitoring device, and the monitoring module communicates with the department-level monitoring device.

20. The method of claim 4, wherein the communication mode comprises at least one of a wireless medical telemetry service (WMTS) mode, a Bluetooth wireless mode, or a Wi-Fi mode.

* * * * *